(12) United States Patent
Ohiso et al.

(10) Patent No.: US 8,956,568 B2
(45) Date of Patent: Feb. 17, 2015

(54) SAMPLE TRANSFER MECHANISM

(75) Inventors: Akihiro Ohiso, Hitachinaka (JP);
Yoshiteru Hirama, Hitachinaka (JP);
Tatsuya Fukugaki, Hitachinaka (JP);
Tetsuya Isobe, Hitachinaka (JP);
Hiroaki Sakai, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 155 days.

(21) Appl. No.: 13/817,547

(22) PCT Filed: Aug. 31, 2011

(86) PCT No.: PCT/JP2011/069723
§ 371 (c)(1),
(2), (4) Date: Mar. 1, 2013

(87) PCT Pub. No.: WO2012/029834
PCT Pub. Date: Mar. 8, 2012

(65) Prior Publication Data
US 2013/0149079 A1 Jun. 13, 2013

(30) Foreign Application Priority Data
Sep. 3, 2010 (JP) .................. 2010-197250

(51) Int. Cl.
*G01N 27/00* (2006.01)
*G01N 31/00* (2006.01)
*G01N 33/00* (2006.01)
(Continued)

(52) U.S. Cl.
CPC ............. *G01N 35/04* (2013.01); *B25J 9/026* (2013.01); *B25J 15/0226* (2013.01); *G01N 35/0099* (2013.01); *B25J 15/10* (2013.01); *G01N 2035/0406* (2013.01)

USPC .................. 422/63; 414/222.13; 414/225.01; 414/618

(58) Field of Classification Search
None
See application file for complete search history.

(56) References Cited

U.S. PATENT DOCUMENTS 6,255,614 B1 7/2001 Yamakawa et al.

FOREIGN PATENT DOCUMENTS

JP 02-259469 A 10/1990
JP 05-162812 A 6/1993
(Continued)

OTHER PUBLICATIONS

International Preliminary Report on Patentability in PCT/JP2011/069723, dated Apr. 18, 2013.

*Primary Examiner* — Jill Warden
*Assistant Examiner* — Julie Tavares
(74) *Attorney, Agent, or Firm* — Mattingly & Malur, PC

(57) ABSTRACT

A sample transfer mechanism of the present invention is characterized broadly by a sample gripping method in which a downward part of a sample vessel is gripped and a cover that achieves an effect as a guide such that gripping arms that grip the sample vessel avoid contact with other objects and bypass surrounding objects, particularly, the sample vessels in approaching and retracting motions. To enhance the effect as the guide and to ensure that the sample vessels can be mounted with a high degree of integration, the shape of the cover and disposition of the sample transfer mechanism are characterized in a number of manners. Thus, a sample transfer mechanism that can perform a transfer process safely with high throughput even under conditions in which a variety of types of sample vessels is mixed together and the sample vessels are mounted with a high degree of integration is provided.

14 Claims, 25 Drawing Sheets

(51) Int. Cl.
*B65H 1/00* (2006.01)
*G01N 35/04* (2006.01)
*B25J 9/02* (2006.01)
*B25J 15/02* (2006.01)
*G01N 35/00* (2006.01)
*B25J 15/10* (2006.01)
*B65G 47/90* (2006.01)

(56) References Cited

FOREIGN PATENT DOCUMENTS

| | | |
|---|---|---|
| JP | 2000-321287 A | 11/2000 |
| JP | 2001-096483 A | 4/2001 |
| JP | 2004-061137 A | 2/2004 |
| JP | 4116206 B2 | 7/2008 |

SAMPLE TRANSFER MECHANISM

TECHNICAL FIELD

The present invention relates to an apparatus for transferring, for example, a sample vessel that houses therein a biological sample, a reagent, or the like.

BACKGROUND ART

A sample transfer mechanism, in other words robotic manipulator assembly, is used by being incorporated in various types of devices that constitute a clinical laboratory automation system (CLAS), such as an in vitro diagnostic (IVD) device and a sample transport and conveying system connected to the IVD device. Various types of tests including biochemical tests, immunological tests, hematologic tests, and polymerase chain reaction assays may be considered as specific examples of IVD. Exemplary IVD devices and their peripheral devices include sample transport and conveying systems used in clinical laboratories, and loading modules, storage modules, and centrifugal modules included in sample preprocessing systems.

The sample transfer mechanism is used for picking up a sample vessel handled by, for example, an IVD device from a holder or the like and transferring the sample vessel onto, for example, another holder or the like. The term "holder or the like" as used herein refers collectively to all parts having a function of holding the sample vessel, including at least all that is collectively called a sample carrier (a sample holder, a sample bucket, a sample rack, a sample tray) and including all that has a function of, in addition to holding the sample vessel, processing (e.g. batch type thermostat) or analyzing (e.g. absorptiometric analysis, fluorescence intensity analysis) the sample with the sample vessel held in place.

A sample transfer mechanism in other words robotic manipulator assembly, includes at least one gripper assembly, a transport mechanism (e.g. an X-Y-Z stage, a robot arm) that moves an entire chuck mechanism horizontally and vertically to a desired location, and a controller that controls the gripper assembly and the transport mechanism.

The gripper assembly includes, as an end effector, a mechanism for grasping and gripping an object (a chuck mechanism) and at least a mechanism for opening and closing the chuck mechanism.

Operation of the sample transfer mechanism is achieved, broadly, by combining basic motions including an X-Y moving motion, an accessing motion, an approaching motion, a retracting motion, an opening motion, a closing motion, a clamping motion, a releasing motion, a picking motion, and a placing motion. These motions will be defined in detail when later describing embodiments.

Recent years have witnessed appearance of, for example, an IVD device that handles a plurality of types of sample vessels and sample vessels having varying lengths are mixed together inside the IVD device. A chuck mechanism for use in such an IVD device is required to have a capability of reliably gripping and transferring the sample vessels having varying lengths. The gripping position appropriate for a specific sample vessel, however, depends on each individual sample vessel that has a unique length, a unique bottom surface shape, a unique cap shape, and the like.

Gripping the sample vessel at a position other than the appropriate gripping position poses such problems as the cap of the sample vessel being gripped (which results in only the cap being removed or unsteady gripping of picking up the sample vessel together with its cap) and a part near an opening portion in the sample vessel that is likely to be contaminated being gripped.

Depending on the length of the sample vessel, conditions are possible in which, in a picking motion, the gripping arm, finger of end effecter is opened and closed at a part of the sample vessel upward of an upper bottom of the sample vessel (specifically, the gripping arm fails to grip the sample vessel) and, in a placing motion, the sample vessel is released, though the sample vessel is not fit in the holder (specifically, the sample vessel is released in the air and falls). The term "appropriate gripping position" as used herein refers to a range on an outer surface of the sample vessel, the range satisfying at least the following conditions:

(1) With the sample vessel mounted steadily in a holder or the like, a portion exposed from the holder or the like that holds the sample vessel in place (an exposed portion);

(2) All gripping arms do not contact the holder or the like during a gripping operation; and (3) The position is away from an area near an opening portion or a cap of the sample vessel.

A related-art technique requires that lowering and raising strokes during a picking motion or a placing motion be previously set for each length of the sample vessel so as to reach the appropriate gripping position and this setting be stored in a controller as a drive pattern. In order to determine the appropriate gripping position for each picking motion for a sample vessel, a method is taken in which the height of the sample vessel is measured or detected for each motion and, based on the result of the measurement, the drive pattern (a stoke in the Z-direction, lowering and raising speed) for an approaching motion and a retracting motion is changed. (See, for example, patent document 1.)

In view of reduction of a risk of contact between the sample vessel or the like and the gripping arm for example, common practice has it that, in related-art sample transfer mechanisms, the drive range in the vertical direction (Z-direction) during the approaching motion and the retracting motion is set such that an area in which a gripping arm 160 is likely to contact the sample vessel is minimized (specifically, an upper portion is gripped).

However, detecting the height of the vessel for each approaching motion reduces throughput of the apparatus.

Moreover, preparing a large number of drive patterns requires that a teaching motion for calibrating the approaching and retracting strokes be performed in a large number of patterns and adjusting the mechanism is likely take a lot of trouble. The "teaching motion" as used herein refers to causing a machine to store, for example, position information or a relation between an operation amount or a control amount and an actual motion of an actuator or other element, or performing calibration.

In addition, the related art offered only poor methods for avoiding the risk of contact between the gripping arm and the sample vessel; specifically, one method is to reduce mounting density of the sample vessel relative to a rack or the like, resulting in low space efficiency, and another is to detect a faulty posture of the sample vessel and thereby to correct the posture of the sample vessel through, for example, moving the gripping arm (see, for example, patent document 2), which results in low time efficiency.

PRIOR ART DOCUMENTS

Patent Documents

Patent Document 1 JP-2004-61137-A
Patent Document 2 JP-04116206-B

SUMMARY OF THE INVENTION

Problem to be Solved by the Invention

As such, in order for the sample transfer mechanism to safely handle sample vessels having different lengths, the gripping position needs to be controlled according to the length of each sample vessel. To achieve that end, a need existed to provide a mechanism or a step for detecting the length of the sample vessel, which posed a problem of increased cost of the mechanism and reduced processing speed of the entire mechanism.

To avoid an accidental contact between the gripping arm and the sample vessel or a harmful effect therefrom (e.g. the gripping arm being caught by a sample vessel during approaching), the related art took approaches with low time or space efficiency, such as, in positions with a risk of contact between the gripping arm and the sample vessel, reducing the lowering and raising speed by a large margin, widening a gap between sample vessels, and correcting posture of the sample vessel through sensor detection.

In view of the foregoing situations, it is an object of the present invention to provide a sample transfer apparatus or mechanism capable of handling sample vessels having different lengths, the sample transfer mechanism offering enhanced safety, high throughput, simpler control method and apparatus configuration, and good maintainability.

Means for Solving the Problem

A sample transfer mechanism according to an aspect of the present invention for solving the foregoing problems is characterized by the following.

Specifically, a sample transfer mechanism comprising at least a gripper assembly 100, a transport mechanism 010, and a controller. The gripper assembly 100 includes a chuck mechanism that includes a plurality of openable gripping arms for gripping an outer wall of a body portion of a sample vessel, the sample vessel having an opening portion, a bottom portion, and the body portion and being available in a plurality of types, and an actuator that opens and closes the chuck mechanism. The transport mechanism 010 moves the gripper assembly 100 in horizontal and vertical direction. The controller controls the chuck mechanism, the gripper assembly, and the transport mechanism 010.

The sample transfer mechanism is characterized in that:

(A) the gripping arms are opened and closed to perform picking and placing motions under a condition in which the gripping arms are lowered to a common portion of an "appropriate gripping position" for all sample vessels to be handled.

The sample transfer mechanism is characterized also by:

(B) a member that covers at least an outside of leading end portions of the gripping arms and has a lower end disposed downwardly of the leading end portions of the gripping arms.

Effects of the Invention

Effects achieved by the sample transfer mechanism according to the present invention will be described based on (A) (hereinafter referred to as characteristic (A)) and (B) (hereinafter referred to as characteristic (B)) of <Means for Solving the Problem>.

The sample transfer mechanism according to the present invention achieves following effects (A1) to (A7) by having the characteristic (A):

(A1) Even if each of the multiple types of sample vessels has the body portion having a unique length that is different from each other, a lowering amount during a picking motion is identical in all sample vessels. This eliminates the need for means for measuring a length of the sample vessel or changing the lowering amount during the picking motion according to a result of measurement of the length. This simplifies an apparatus configuration and control method.

(A2) Of the body and a lower bottom of the sample vessel, the length of a portion gripped by the gripping arms is substantially identical without regard to the type of sample vessel. This eliminates the need for changing the lowering amount during the placing motion according to the length of the sample vessel, thus simplifying a control method.

(A3) At least, time required for detecting the length of the sample vessel (about 0.2 seconds to 1 second depending on chattering and other reason) is not required, which is advantageous for improving throughput. (For example, a sample transfer mechanism having a transfer speed of 800 samples/h takes 4.5 seconds for transferring one sample vessel. Suppose that time required for transferring one sample increases to 5.0 seconds from 4.5 seconds. Then, the throughput is reduced down to 720 samples/h. Hence, time of about 0.2 seconds to 1 second should be considered to be extremely long.)

(A4) A reduced number of motion patterns decreases the number of patterns of teaching motions, facilitating maintenance.

(A5) A downward part of the sample vessel is gripped, which shortens a distance between the gripping position at which the sample vessel is gripped and the lower bottom of the sample vessel. This enables accurate positioning during a placing motion.

(A6) The short distance between the gripping position at which the sample vessel is gripped and the lower bottom of the sample vessel eliminates likelihood that torque arising from, for example, a pushing force to push a sample vessel into a holder or the like will be applied hard to the gripping position. The sample vessel can therefore be pushed into a holder container safely.

(A7) The gripping arms 160 grip a part near the opening portion or a cap, which avoids a situation in which a sample sticks to the gripping arms 160 or the gripping arms 160 fail to grip any sample vessel.

The characteristic (A) achieves the following additional effects by further having the characteristic (B):

(B1) During an approaching motion, there is no contact between the gripping arms and the sample vessel to be accessed, or between the gripping arms and a surrounding sample vessel.

(B2) A cover 150, if not the gripping arms, may contact the sample vessel to be accessed or a surrounding sample vessel; however, the cover 150 has a leading end and an outer wall that are smoother than the gripping arms, which reduces a risk involved in the contact.

(B3) The cover 150 has an effect of making its way to bypass objects (sample vessels in particular) surrounding the sample vessel to be approached or retracted during the approaching or retraction motion by the chuck mechanism. This permits raising and lowering motion at a speed higher than in the related-art chuck mechanism (no harmful effect even from a raising and lowering motion at higher speeds), so that throughput can be improved.

(B4) The cover 150 functions to guide the gripper assembly even for a holder in which sample vessels are densely held. This facilitates gripping at the downward part of the sample vessel.

(B5) Should the chuck mechanism contact a surrounding sample vessel or the like during an open/close operation of the gripping arms, there is no risk that the opening or closing gripping arms will flick a surrounding sample vessel or the like.

(B6) As a result of (B5) above, making opening and closing of the gripping arms at higher speed does not produce any harmful effect, so that the opening and closing operation of the gripping arms can be made faster.

(B7) A risk that the gripping arms will contact a surrounding sample vessel to break its posture is considerably reduced.

(B8) Even if a sample vessel is held in the holder in a tilted position, the cover 150 can correct posture of the sample vessel, so that the chuck mechanism can clamp the sample vessel in a position substantially perpendicular to the holder.

MODES FOR CARRYING OUT THE INVENTION

Preferred embodiments of the present invention will be described in detail below.

Figure 1:
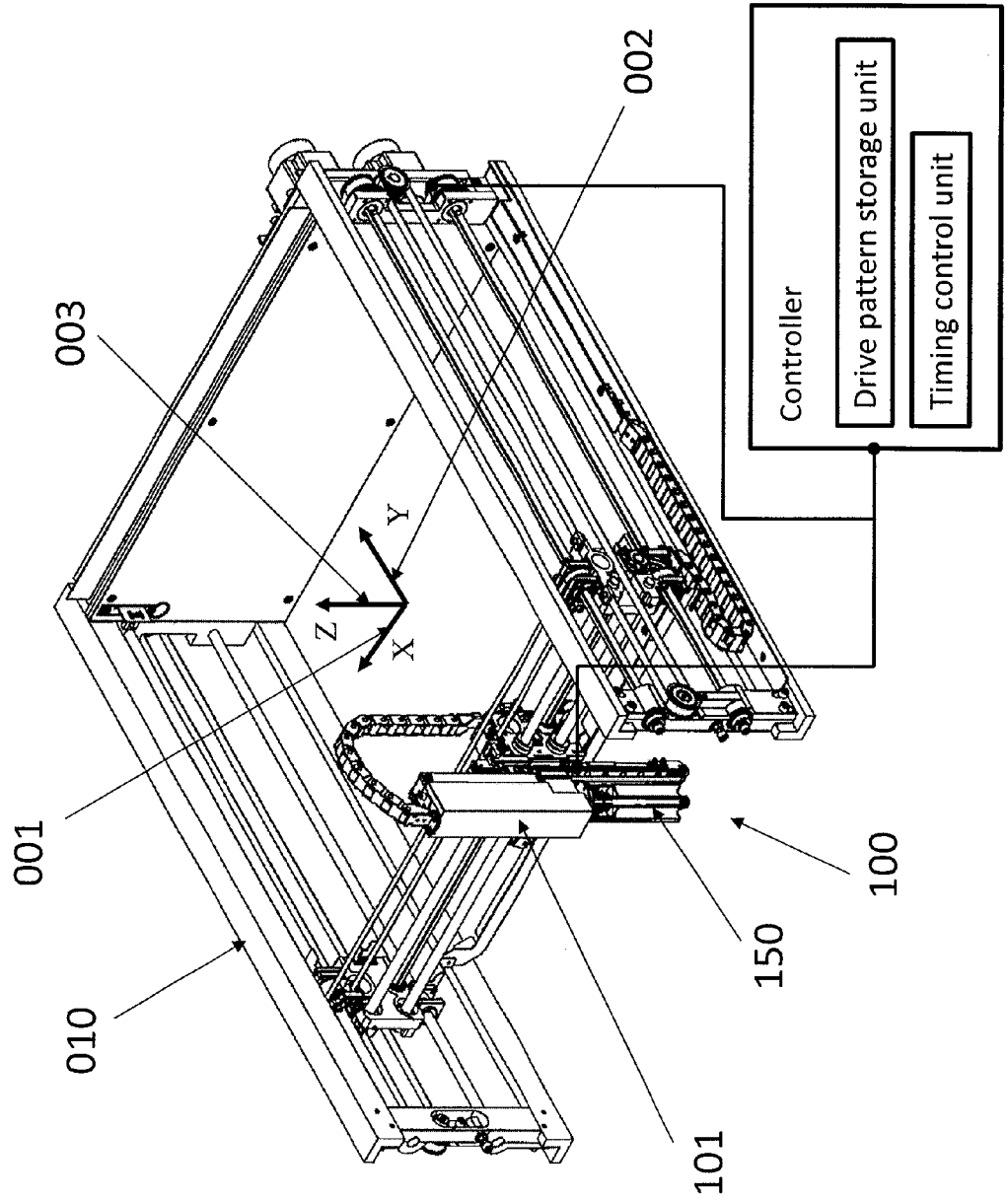
FIG. 1 shows a main section of a sample transfer mechanism according to an embodiment of the present invention.

General Configuration of Sample Transfer Mechanism According to an Embodiment of the Present Invention FIG. 1 shows generally a sample transfer mechanism according to an embodiment of the present invention. The sample transfer mechanism includes a gripper assembly 100, a transport mechanism 010 that moves the gripper assembly 100 horizontally and vertically, and a controller that controls operation of the gripper assembly 100 and the transport mechanism 010.

The transport mechanism 010 of the sample transfer mechanism according to the embodiment is an X-Y-Z stage that moves the gripper assembly 100 in three directions of an X-direction 001, a Y-direction 002, and a Z-direction 003. This is, however, not the only possible arrangement; alternatively, for example, a robot arm or the like may be incorporated, as long as the sample transfer mechanism is configured so as to capable of moving the gripper assembly to any desired position.

The controller controls each of actuators of the sample transfer mechanism independently and includes at least a drive pattern storage unit and a timing control unit. Specifically, the drive pattern storage unit stores drive patterns for achieving each of basic motions listed below. The timing control unit ensures that motions are performed sequentially based on a corresponding driven pattern.

X-Y moving motion: Moving a chuck mechanism in an X-Y direction with the transport mechanism 010 (the X-Y direction extending in parallel with the horizon).

Accessing motion: X-Y moving motion moving the chuck mechanism to a position immediately above a specific sample vessel mounting portion on a sample rack or the like (the position at which a central axis of the chuck mechanism substantially is aligned with a central axis of the sample vessel mounting portion).

Approaching motion: Lowering the chuck mechanism in the Z-direction (the direction perpendicular to the horizon) to thereby cause the chuck mechanism approach a specific sample vessel mounting portion; the approaching motion is enabled only after the chuck mechanism has been accessed to a specific sample vessel mounting portion.

Retracting motion: Raising the sample transfer mechanism that has approached a specific sample vessel mounting portion in the Z-direction.

Opening motion: Changing a position of a gripping arm from a closed position to an open position.

Closing motion: Changing the position of the gripping arm from the open position to the closed position.

Clamping motion: Causing the chuck mechanism to close and clamp a specific sample vessel or the like.

Releasing motion: Causing the chuck mechanism to open and release a previously clamped sample vessel.

Picking motion: Approaching a specific sample vessel mounting portion with the gripping arm open and removing a sample vessel mounted in the sample vessel mounting portion.

Placing motion: Causing the chuck mechanism that holds a sample vessel to approach a specific sample vessel mounting portion and to mount the sample vessel on the sample vessel mounting portion.

General Arrangements of Gripper Assembly

Figure 2:
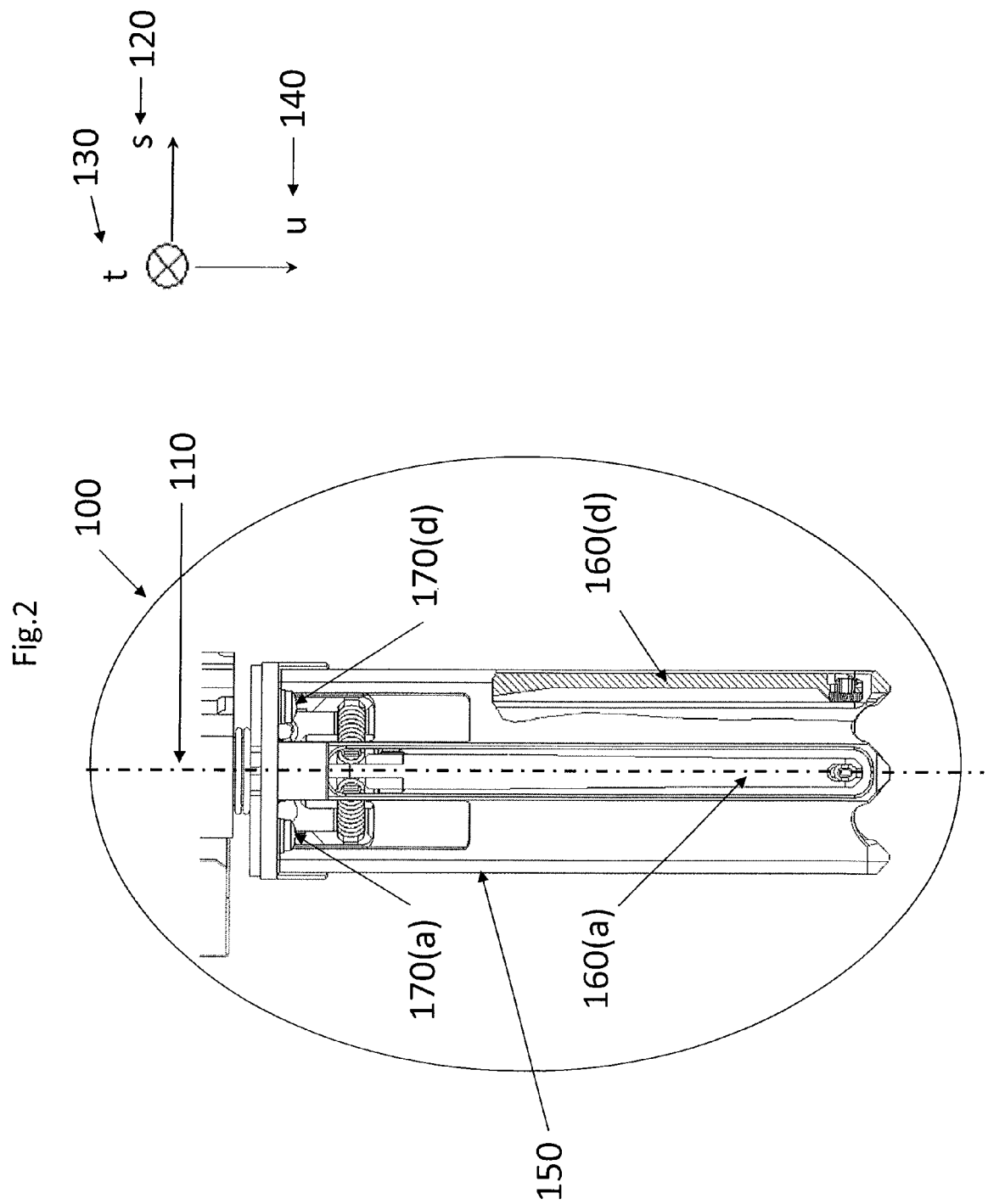
FIG. 2 shows a main section of a gripper assembly of the sample transfer mechanism according to the embodiment of the present invention.
Figure 3:
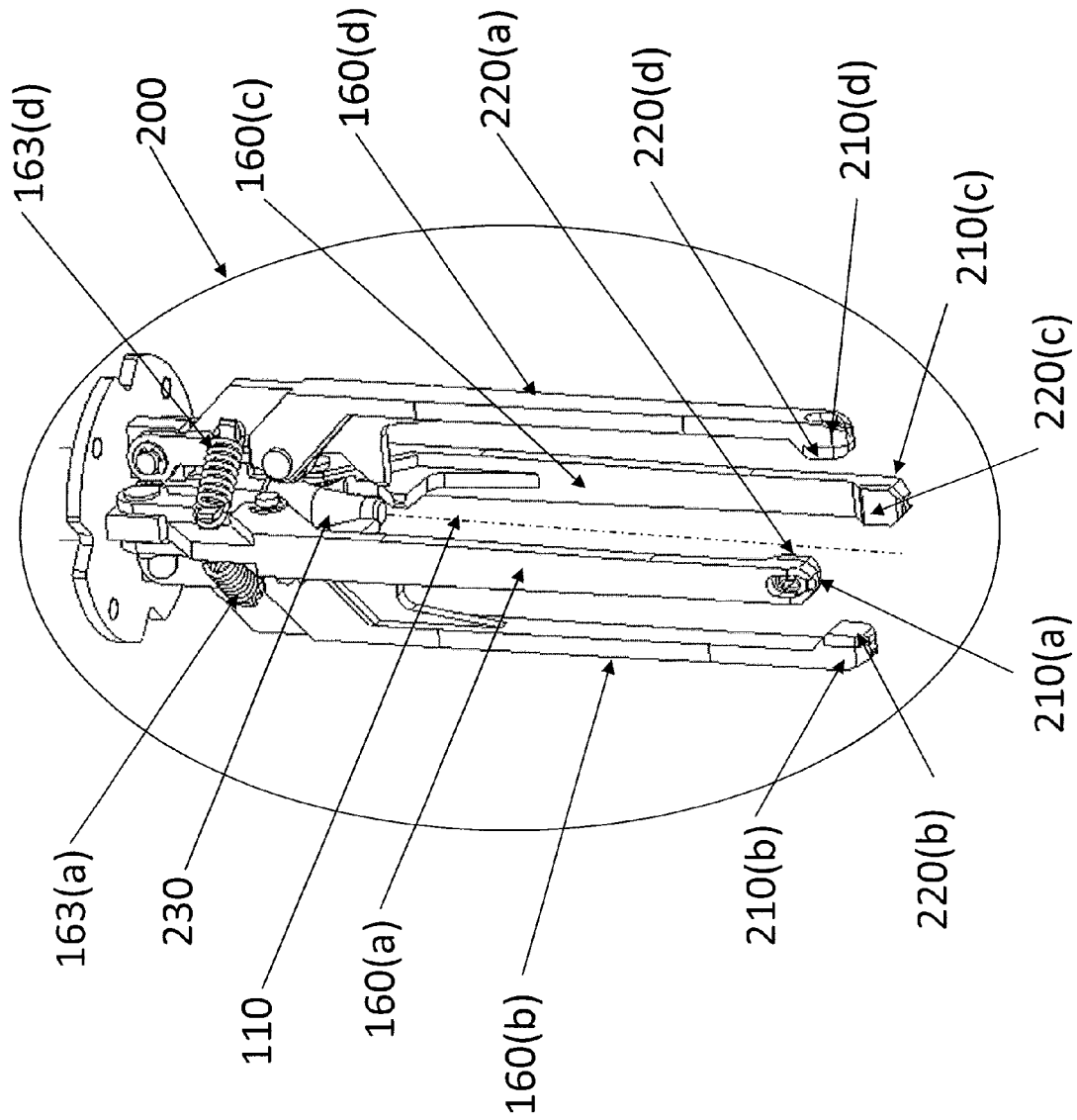
FIG. 3 is an outline view showing a chuck mechanism according to the embodiment of the present invention.
Figure 4:
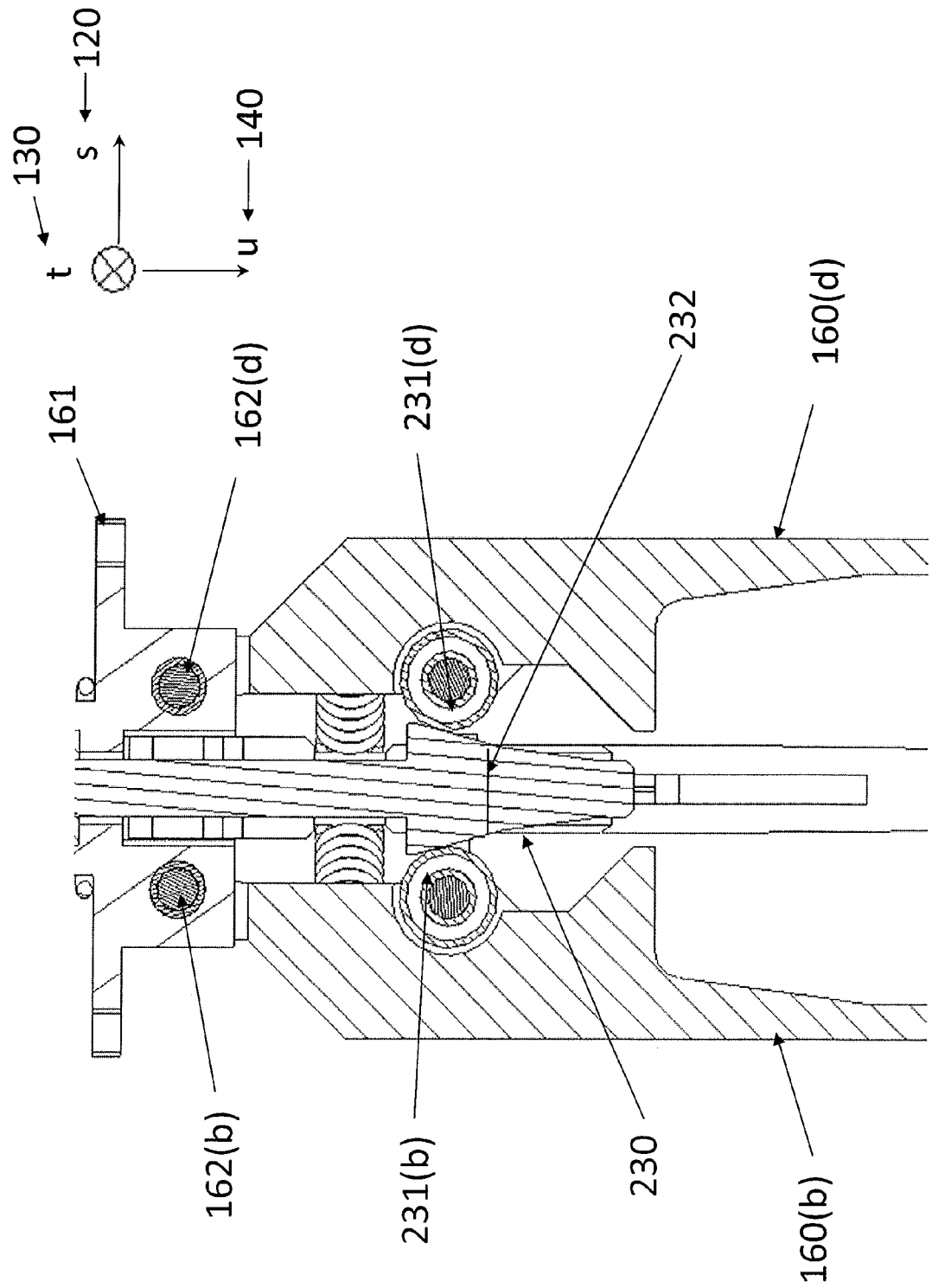
FIG. 4 shows an open/close mechanism of the chuck mechanism according to the embodiment of the present invention.

FIG. 2 shows, using a partial cross-sectional view, a front elevational view of the gripper assembly 100 of the sample transfer mechanism according to the embodiment of the present invention. FIGS. 3 and 4 show a chuck mechanism of the gripper assembly 100.

The gripper assembly 100 according to the embodiment of the present invention mainly includes a chuck mechanism 200, a base section 101, and a cover 150. Specifically, the chuck mechanism 200 clamps the sample vessel. The base section 101 supports the chuck mechanism 200 and is connected to the transport mechanism 010. The cover 150 covers an outside of the chuck mechanism 200.

The chuck mechanism includes at least a plurality of (four in this embodiment) gripping arms 160(a), (b), (c), (d), a fixture 161 that connects all of the gripping arms to the base section 101, a translation cam 230, and springs 163(a), (b), (c), (d) corresponding in number with the gripping arms.

To describe a structure of the gripper assembly 100 hereafter, three directions of an s-direction 120, a t-direction 130, and a u-direction 140 will be defined. The s-direction 120, the t-direction 130, and the u-direction 140 are defined to form a left-handed system and a downward direction of the s-direction 120 is defined to be positive.

The chuck mechanism according to the embodiment of the present invention has an axially symmetrical shape. A datum axis (a central axis 110 of the gripper assembly) that represents symmetry of the chuck mechanism coincides with the s-direction.

The cover also has an axially symmetrical shape. The cover 150 is assembled in the gripper assembly 100 such that a central axis 300 of the cover coincides with the central axis 110 of the gripper assembly. In this embodiment, the cover is screwed to the fixture 161 of the chuck mechanism 200 using screws 170(a) to (d) and is thereby assembled in the gripper assembly 100 via the fixture 161.

The base section 101 of the gripper assembly 100 has a mechanism for opening and closing the gripping arms 160 of the chuck mechanism 200 (actuators and other parts not shown).

In addition, the gripper assembly 100 is assembled relative to the X-Y-Z stage 010, more specifically, such that the u-direction 140 extends in parallel with and opposite to the Z-direction 003 and the s-direction 120 and the t-direction 130 form an angle of 45 degrees relative to the X-direction 001 and the Y-direction 002, respectively.

Structure of Chuck Mechanism

The gripping arms 160(a), (b), (c), (d) are disposed symmetrically about the central axis 110 of the gripper assembly. When the chuck mechanism 200 is viewed from below, the gripping arms 160(a), (b), (c), (d) are disposed in sequence in a counterclockwise direction such that 160(a) and (c) face each other and 160(b) and (d) face each other.

Additionally, the fixture 161 that connects the gripping arms to the base section 101 is mounted so as to extend perpendicularly to the s-direction 120.

In addition, the fixture 160 and the gripping arms 160(a), (b), (c), (d) are each movably connected to the fixture 161 at a corresponding one of positions 162(a), (b), (c), (d) so as to be swingable about 162(a), (b), (c), (d). Specifically, the gripping arms 160(a), (b), (c), (d) each have a portion near an upper distal end connected to the fixture 161, the connection being connected so as to form a joint structure having at least one degree of freedom.

The translation cam 230 that extends in the u-direction 140 from the base section 101 moves vertically along the central axis 300 of the cover in the u-direction 140 and the base section 101 includes a solenoid (not shown) as a mechanism for pushing the translation cam 230. 160(a), (b), (c), (d) include ring-shaped followers 231(a), (b), (c), (d), respectively, each of the followers being in contact with the translation cam at all times. The gripping arm 160(b) and the gripping arm 160(d) open and close in a direction that coincides with the s-direction 120 and the gripping arm 160(a) and the gripping arm 160(d) open and close in a direction that coincides with the t-direction 130.

The chuck mechanism further includes the spring 163(a) that connects the gripping arm 160(a) and the gripping arm 160(b), the spring 163(b) that connects the gripping arm 160(b) and the gripping arm 160(c), the spring 163(c) that connects the gripping arm 160(d) and the gripping arm 160 (c), and the spring 163(d) that connects the gripping arm 160(d) and the gripping arm 160(a). An elastic force of each of these springs applies at all times force acting in a closing direction to the gripping arms 160.

Opening of the gripping arms 160 is achieved when the translation cam 230 lowers to push open the gripping arms 160. Holding of the gripping arms 160 in their opened positions is achieved by bringing the translation cam 230 to a stop at a position at which the gripping arms 160 are fully open. A feed amount of the translation cam 230 is set such that the translation cam 230 is brought to a stop when the gripping arms 160 are placed in a substantially vertical position. An open/close mechanism of the gripping arms 160 is achieved such that the gripping arms 160 are placed in a substantially vertical position when the gripping arms 160 are fully opened.

While in related-art arrangements, the translation cam has a substantially trapezoidal cross section, the translation cam 230 has a shoulder 232 so that an open/close angle per unit lower/raise amount of the translation cam is greater at greater openings of the gripping arms 160.

In the embodiment of the present invention, a solenoid actuator (not shown) mounted inside the base section 101 gives a drive force to operate the translation cam 230 to thereby open or close the gripping arms 160. The open/close operation can therefore be achieved by simply energizing or de-energizing the solenoid actuator.

Structure of Cover

Figure 5:
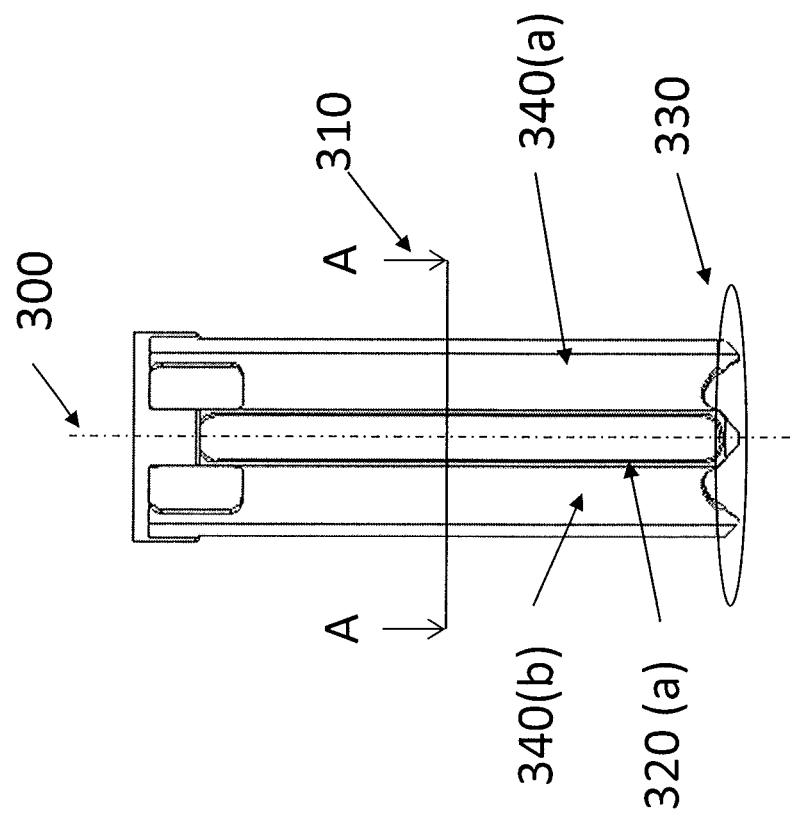
FIG. 5 is a front elevational view showing a cover according to the embodiment of the present invention.
Figure 6:
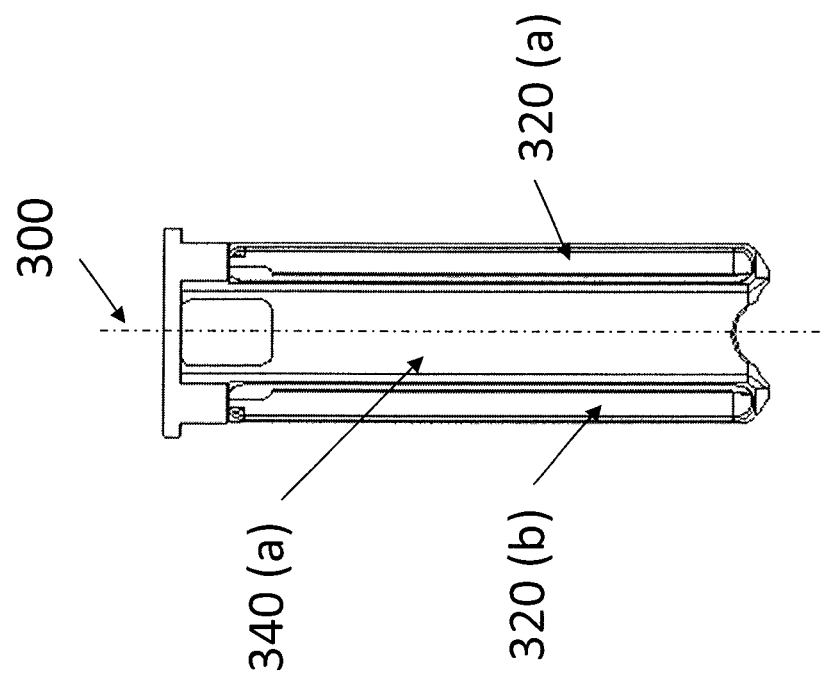
FIG. 6 is a view as looking straight at the cover shown in FIG. 5 rotated 45 degrees counterclockwise.
Figure 7:
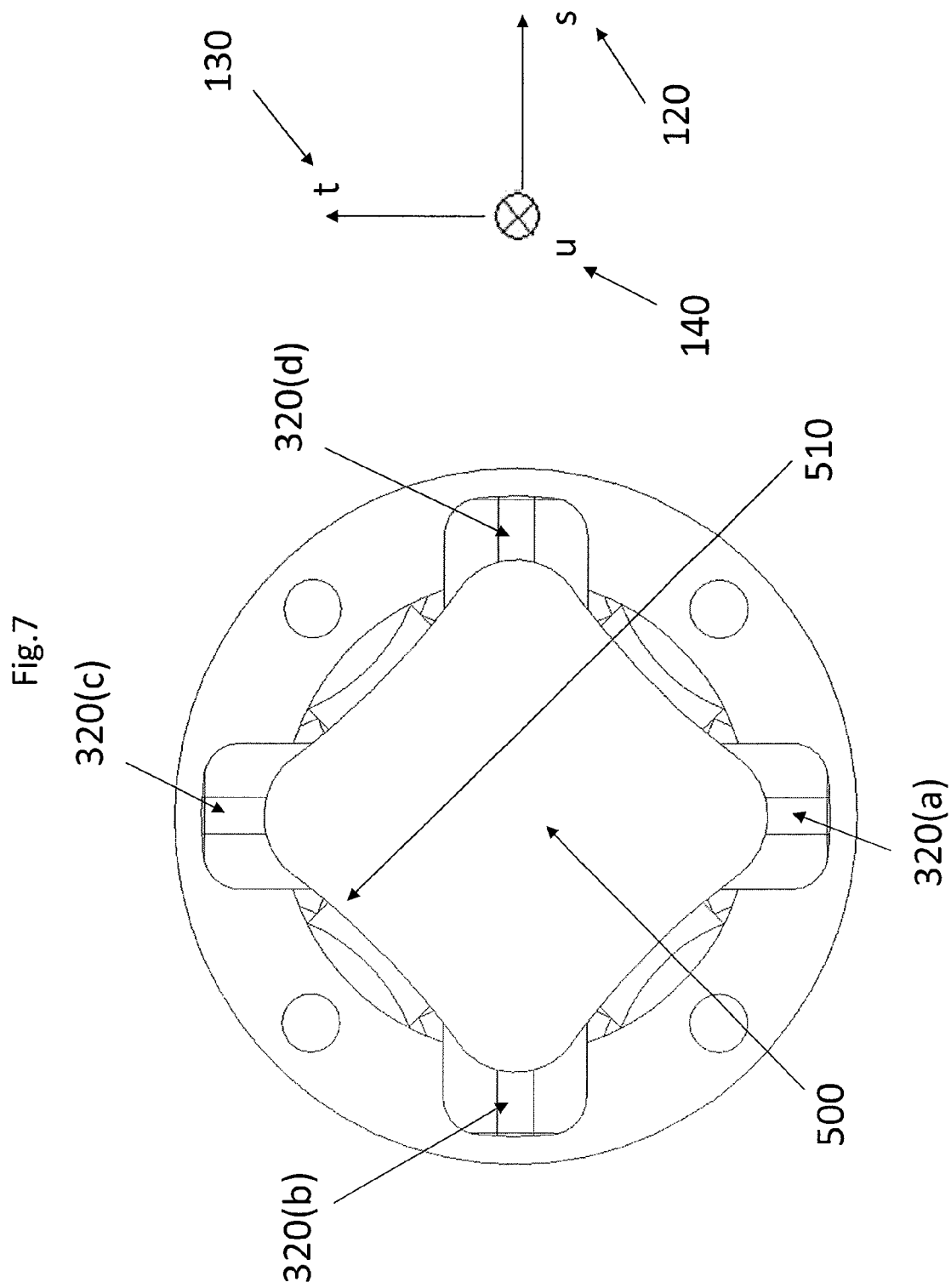
FIG. 7 is a plan view showing the cover according to the embodiment of the present invention.
Figure 8:
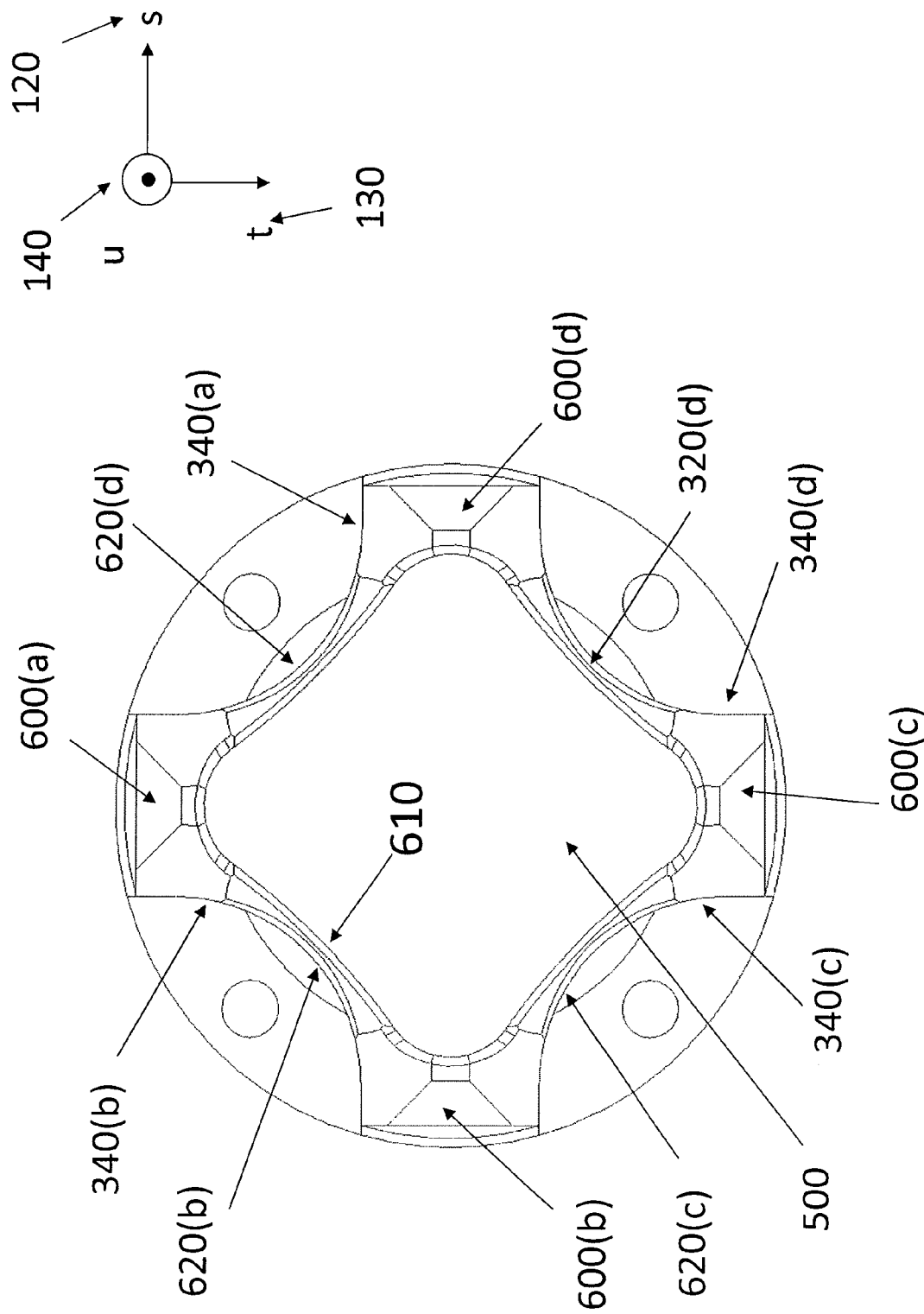
FIG. 8 is a bottom view of the cover according to the embodiment of the present invention.
Figure 9:
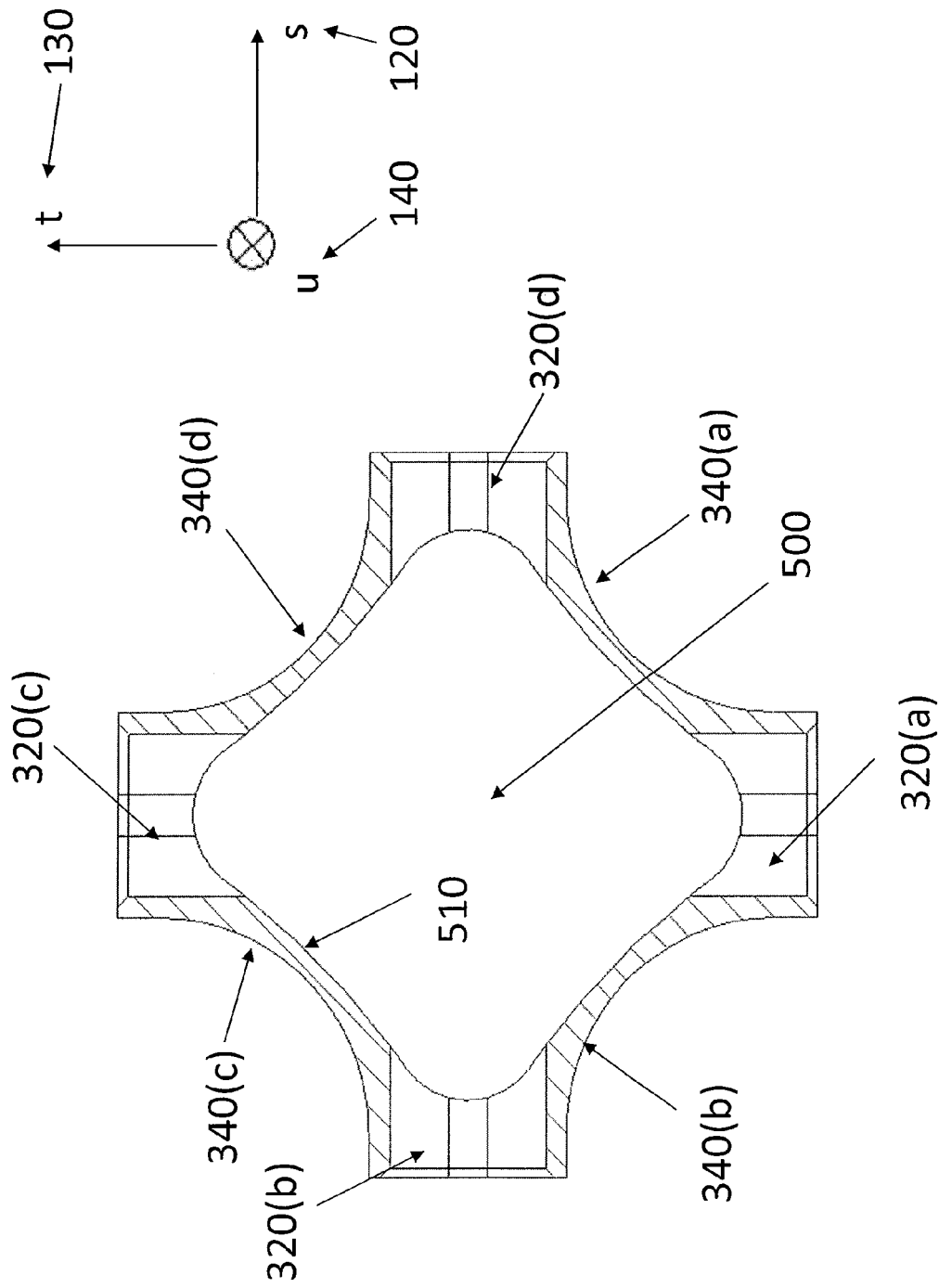
FIG. 9 is a cross-sectional view of the cover taken along line A-A of FIG. 5.

FIG. 5 is a front elevational view showing the cover 150 according to the embodiment of the present invention. FIG. 6 is a view as looking straight at the cover shown in FIG. 5 rotated 45 degrees counterclockwise about the central axis 110 of the gripper assembly 100. FIG. 7 is a plan view showing the cover 150. FIG. 8 is a bottom view of the cover according to the embodiment of the present invention. FIG. 9 is a cross-sectional view of the cover taken along line A-A 310.

The cover 150 of the present invention is formed symmetrically about the central axis 300. The cover 150 may be formed as an integrated part by turning or otherwise machining a bar stock of aluminum or other metal. The cover 150 may also be molded from, for example, metal or resin, or may still be an assembly incorporating a plurality of parts.

The chuck mechanism 200 may be fixed so as to have predetermined play therein so as to be when external force were subjected, that joint are slightly flex to springy branches the external force, relative to the X-Y-Z stage 010 longitudinally and laterally and to flex plastically about several millimeters when pressed perpendicularly to the central axis 300 of the cover at a part thereof near an opening portion 330 of the cover.

The cover 150 of the present invention is fixed to the chuck mechanism 200 with a screw 170 such that the central axis 300 of the cover coincides with the central axis 110 of the sample transfer mechanism.

The structure of the cover 150 will be described below. The cover 150 has an axially symmetrical shape and is assembled to the gripper assembly 100 such that the central axis 300 of the cover coincides with the central axis 110 of the gripper assembly. The three directions of the s-direction 120, the t-direction 130, and the u-direction 140 will therefore be also used when describing the shape of the cover.

The cover of the present invention, when mounted in the gripper assembly 100, has thereinside a hollow 500 that can house a sample vessel therein.

The cover 150 is also formed such that, when the cover 150 is mounted in the gripper assembly 100, a leading end of the cover 150 is disposed downwardly of a leading end of the gripping arms 160.

The cover 150 has the opening portion 330 at its lower end. The opening portion 330 has a notched leading end, each notch being rounded. Possible shapes include, in combination, several-millimeter chamfered (e.g. 600(a) to (d)) or radiused (on the inside) 610, or radiused (on the outside) (e.g. 620(a) to (d)).

The cover 150 further has grooves 320(a) to (d) that correspond in number at least with the gripping arms 160, formed in an inner wall thereof. The grooves 320(a) to (d) are formed such that, with the cover 150 mounted in the gripper assembly 100, the gripping arms 160 fit thereinto when the gripping arms 160 are opened.

Specifically, the grooves 320(a) to (d) extending downwardly are formed so as to be disposed symmetrically about the central axis 300 and equidistantly from each other. The grooves 320(a) to (d) are formed such that 320(a) and (c) face each other, 320(b) and (d) face each other, a direction extending from 320(b) to 320(d) is the s-direction 120, and a direction extending from 320(a) to 320(c) is the t-direction 130. Additionally, the grooves do not extend up to the lower end 330 of the cover.

Recesses 340 are similarly disposed symmetrically about the central axis 300 of the cover and equidistantly from each other and formed to extend vertically along the cover 150. The recess 340, in particular, extends up to the lower end of the cover. The recesses 340 are also formed such that a direction extending from an apex of a recess 340(b) to an apex of 340(d) forms an angle of 45 degrees relative to the s-direction 120 and a direction extending from an apex of a recess 340(a) to an apex of 340(c) forms an angle of 45 degrees relative to the s-direction 120. It is noted that the term "apex" of each recess refers to a position in a ridge of the recess 340 recessed most (a position farthest away inwardly from a circumscribed circle of the cover) in a vertical cross section (a cross section perpendicular to the u-direction 140) of the cover 150.

Gripping Position of Sample Vessel

Figure 10:
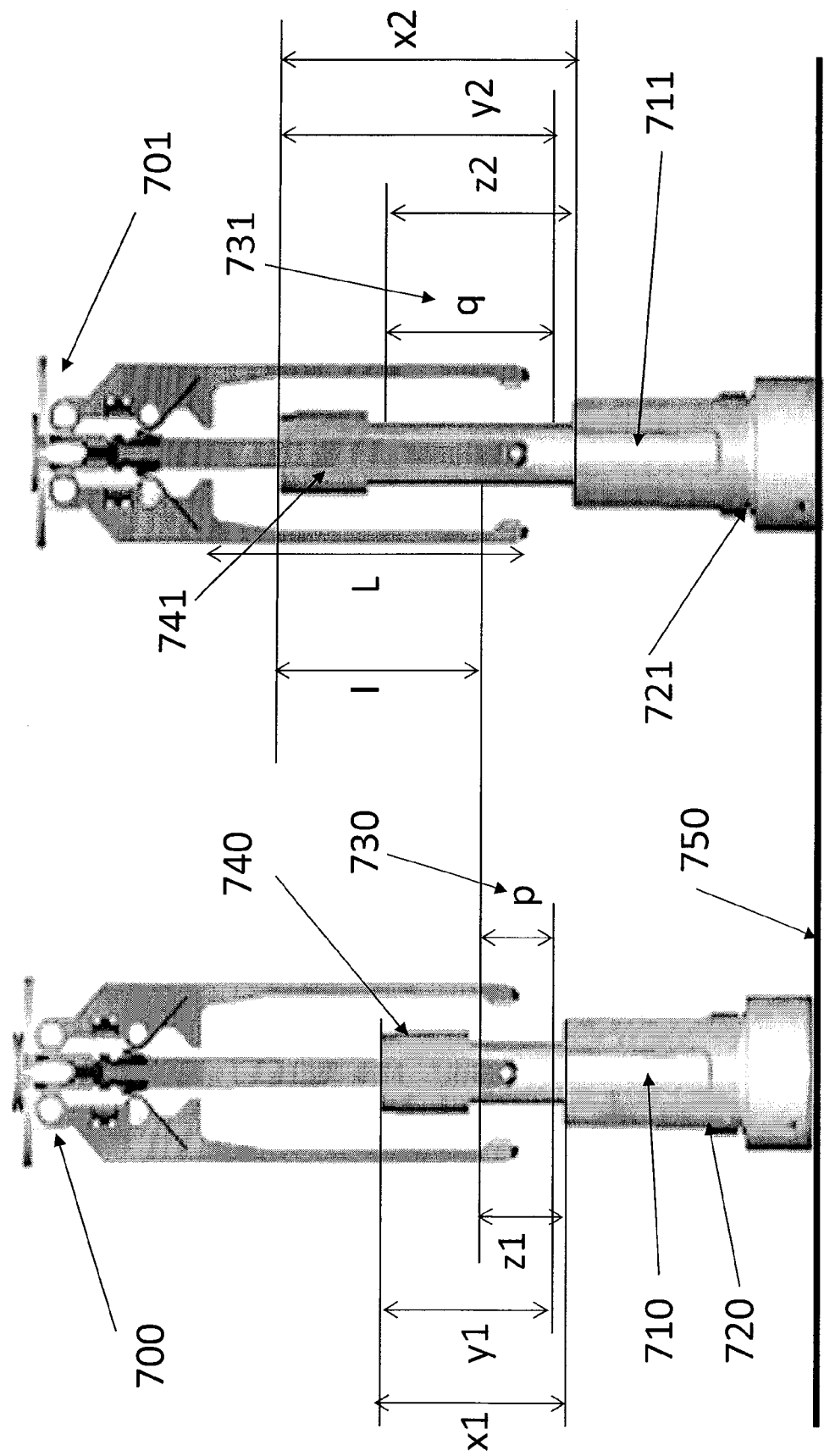
FIG. 10 is a schematic view for illustrating a gripping position of the chuck mechanism according to the present invention.
Figure 11:
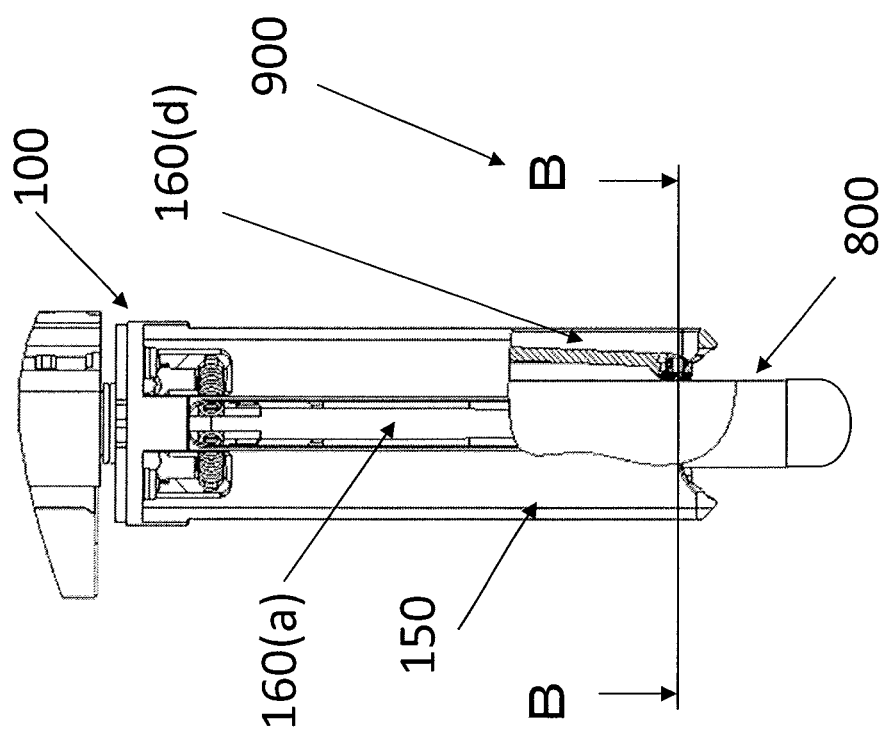
FIG. 11 is a partial cross-sectional view showing a condition in which the chuck mechanism clamps a sample vessel.
Figure 12:
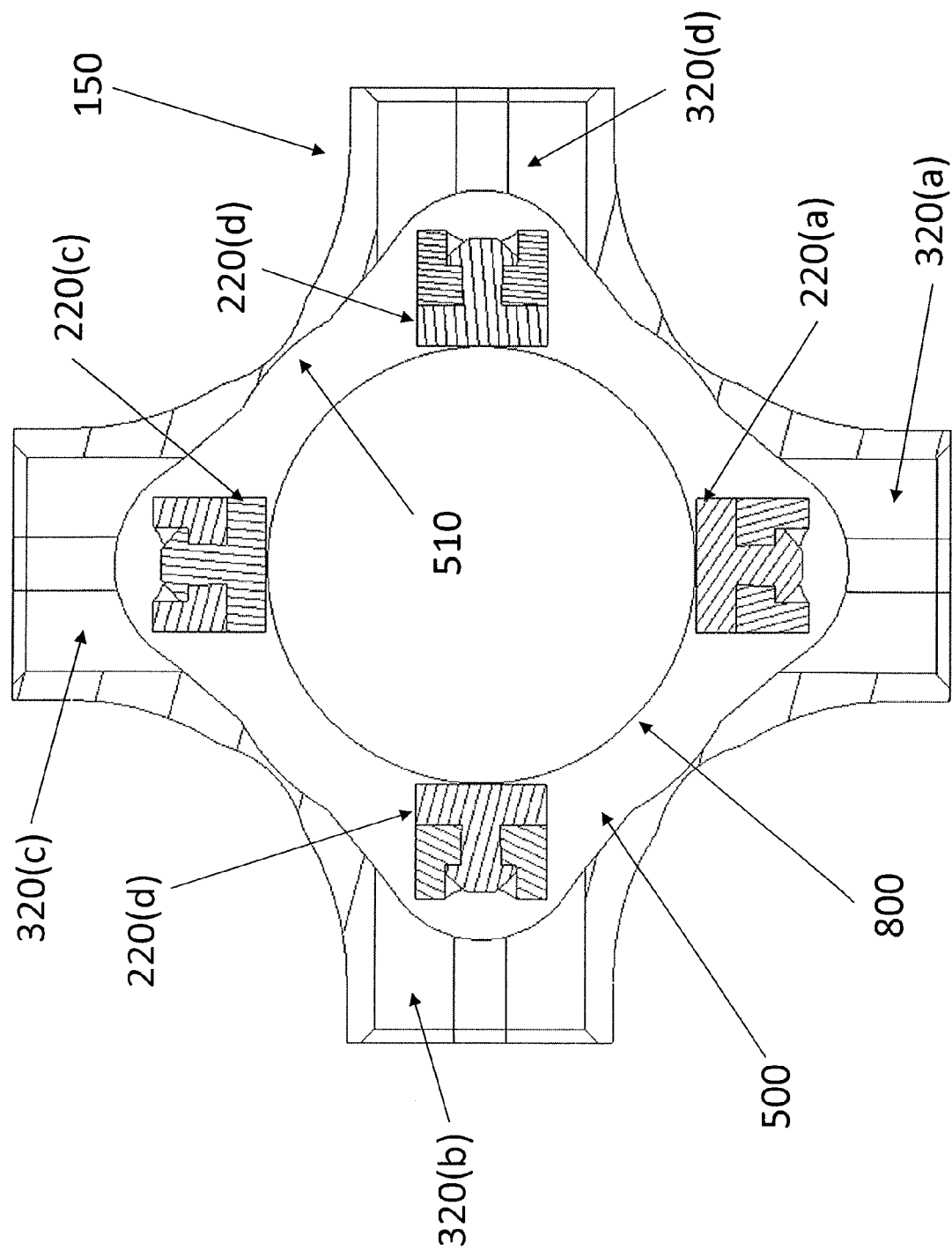
FIG. 12 is a cross-sectional view taken along line B-B of FIG. 11.
Figure 13:
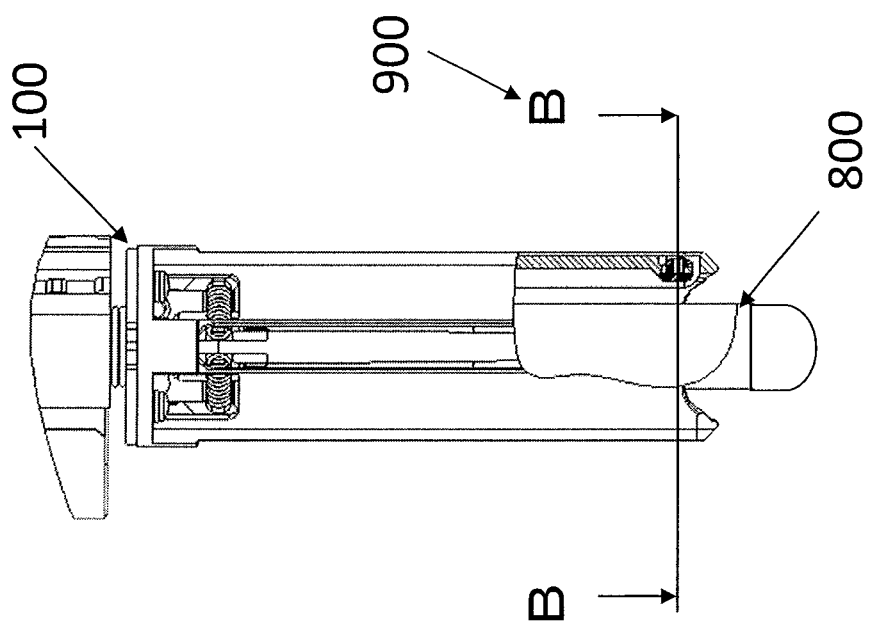
FIG. 13 is a partial cross-sectional view showing a condition in which the chuck mechanism releases a sample vessel.
Figure 14:
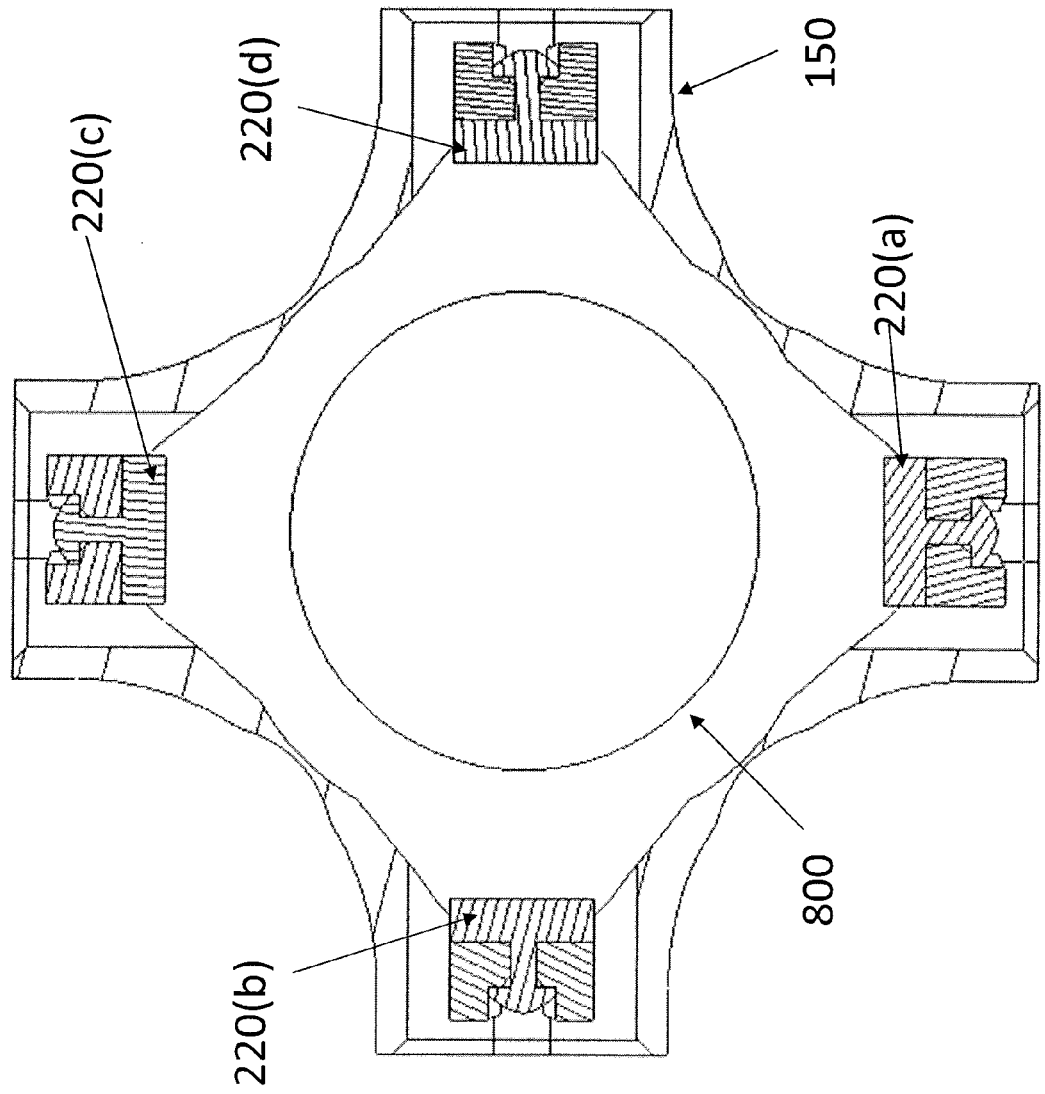
FIG. 14 is a cross-sectional view taken along line B-B of FIG. 13.

FIG. 10 is a schematic view for illustrating a gripping position of the chuck mechanism taught in a teaching motion according to the present invention, in which a short sample vessel 710 and a long sample vessel 711 are mounted in single-vessel transport holders 720, 721, respectively, disposed on the same reference surface. The short sample vessel and the long sample vessel are capped with caps 740, 741, respectively. For ease of viewing, FIG. 10 shows the gripper assembly 100 from which the cover 150 has been removed.

Gripping positions of the short sample vessel 710 and the long sample vessel 711 in the present invention are schematically shown in FIG. 10. The "gripping position" refers to an area on an outer surface of a sample vessel body, which satisfies all of the following conditions (1) to (3):

(1) The area is exposed from a holder or the like that holds the sample vessel;

(2) The gripper assembly 100 does not contact the holder or the like during the gripping operation; and (3) The area is away from portions near the opening portion in, or the cap of, the sample vessel.

Of the above conditions, the exposed length of the condition (1) is uniquely determined from, for example, an overall length of the sample vessel, and the shapes of the bottom surface and the holder.

An area x1 corresponds to this for the short sample vessel 710, and an area x2 corresponds to this for the long sample vessel 711.

The condition (2) means that the lower end of the gripping arm 160 is away several millimeters from an upper surface of the holder that holds the sample vessel and the requirement is uniquely determined by the shape of the holder. An area y1 and an area y2 correspond to this for the short sample vessel 710 and the long sample vessel 711, respectively.

The condition (3) applies to a case in which part of the cap is exposed to the outside of the sample vessel (e.g. an outer gird is provided or a screw cap is used), in consideration of the shape and size of the cap mounted on the sample vessel that can be used in the chuck mechanism. The condition means that a protrusion 210 of the gripping arm 160 is away several millimeters from the portion of the cap exposed to the outside, specifically, the part of the cap covering the surface of the sample vessel in a skirt-like manner. An area z1 and an area z2 correspond to this.

From the foregoing, the areas that satisfy all of the conditions (1) to (3) are established for the respective sample vessels. Specifically, an area p 730 representing an overlap of x1 to z1 is set for the short sample vessel 710 and an area q 731 representing an overlap of x2 to z2 is set for the long sample vessel 711.

The chuck mechanism finds an area that satisfies the above-mentioned conditions (1) to (3) for each of the longest sample vessel and the shortest sample vessel out of all sample vessels to be handled. The chuck mechanism then defines an area common to the two areas to be the appropriate gripping position and sets a downward stroke during, for example, the approaching motion so that the protrusions 210 of all gripping arms 160 are positioned at a height corresponding to the appropriate gripping position. In FIG. 10, the overlap area of the area p 730 and the area q 731 is the area p 730. Therefore, if the sample vessel having the shortest exposed portion out of all sample vessels to be handled is the sample vessel 710, then the gripping arms 160 have only to be lowered to a height at which the area p 730 can be gripped and grip the sample regardless of which specific sample vessel is being handled. If there is any other short sample vessel having a short exposed portion, a similar examination has only to be made based on the assumption that the other short sample vessel is the short sample vessel, specifically, the short sample vessel 710 shown in FIG. 10.

Determining the gripping position of the chuck mechanism through the foregoing method results in the sample vessel being gripped at a position lower than in the related-art arrangements, excepting the shortest sample vessel. To prevent the upper end of the cap or the opening portion of the sample vessel from contacting part of the gripper assembly, such as the gripping arms 160 or the gripping arm open/close mechanism (the cam-follower mechanism according to the present invention), preferably, each of the gripping arms 160 has a length L that is longer than the length of the following expression (L-I), specifically, (length of (1) of the longest sample vessel x1)–(a gripping position l).

If a cap of the sample vessel is screwed into an inside of the sample vessel and no part of the cap covers the surface of the sample vessel, such as an ordinary rubber cap, or if the sample vessel is not capped at all, preferably, the similar examination is made for a case in which a cap exposed to the outside is mounted.

An optimum gripping position is determined in advance at the time of designing the sample transfer mechanism and added or updated as necessary at the time of maintenance.

Shape of Gripping Arm

Protrusions 210(a) to (d) are formed at the leading ends of the gripping arms 160. The protrusions 210(a) to (d) are pressed against the surface of the body portion of the sample vessel when the sample vessel is to be gripped. In addition, to ensure that the sample vessel is to be gripped reliably, rubber members 220(a) to (d) having a large coefficient of friction are mounted at portions of the protrusions 210(a) to (d) gripping the sample vessel, thereby preventing the sample vessel from slipping to fall or preventing similar fault.

The length of the gripping arm 160 is characterized by being longer than the upper bottom portion of the sample vessel because of the gripping position in the downward gripping condition.

Exemplary Mounting in IVD Device or the Like

Figure 25:
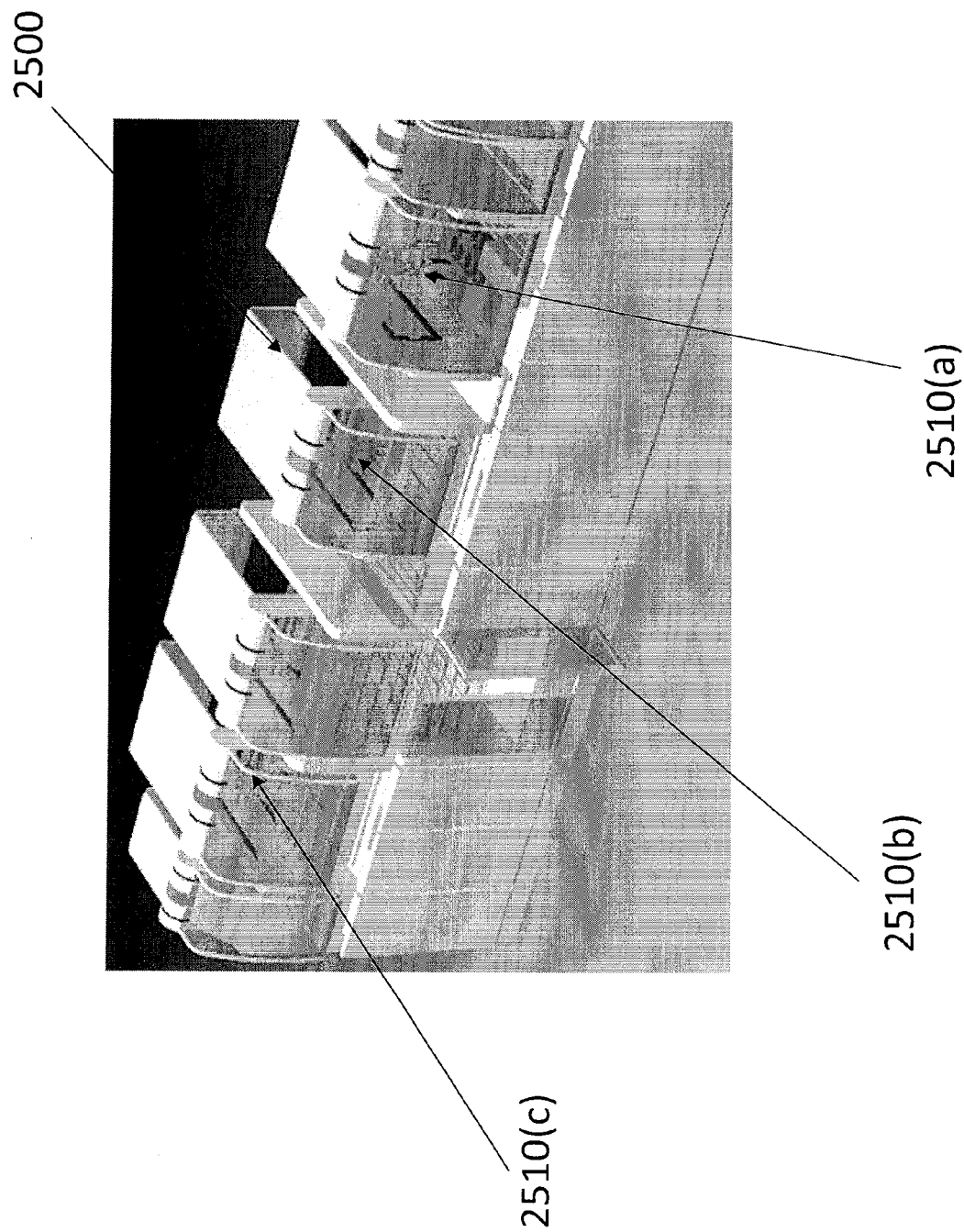
FIG. 25 shows exemplary mounting of the sample transfer mechanism according to the present invention.

FIG. 25 shows exemplary mounting of the sample transfer mechanism according to the embodiment of the present invention. FIG. 25 shows the sample transfer mechanism according to the present invention incorporated in a sample preprocessing system that performs a series of processes for sample vessels loaded therein, including cap opening, centrifugal separation, sub-sample dispensing, and capping.

The sample transfer mechanism according to the present invention can be incorporated into various types of units that need to transfer sample vessels among a holder, a tray, and a bucket, including a sample loading unit 2510(b) that transfers a large number of sample vessels on a tray loaded therein onto a sample transport holder, a centrifugal separation unit 2510(a) that transfers the sample vessels transported on the holder onto a bucket for centrifugal separation, and a storage unit 2510(c) that picks up sample vessels that has undergone the processing and places them on a storage tray. Additionally, the sample transfer mechanism according to the present invention is provided as the gripper assembly 100 integrated with the X-Y-Z stage as shown in FIG. 1, which permits easy incorporation into various types of devices. It is noted that the controller for the sample transfer mechanism according to the present invention may serve also for the sample preprocessing system or each individual unit.

First Embodiment

A first embodiment of the present invention will be described below for an exemplary picking motion performed by the sample transfer mechanism according to the present invention, out of an operation in which the sample transfer mechanism transfers a sample vessel from a sample rack onto another sample rack.

Figure 16:
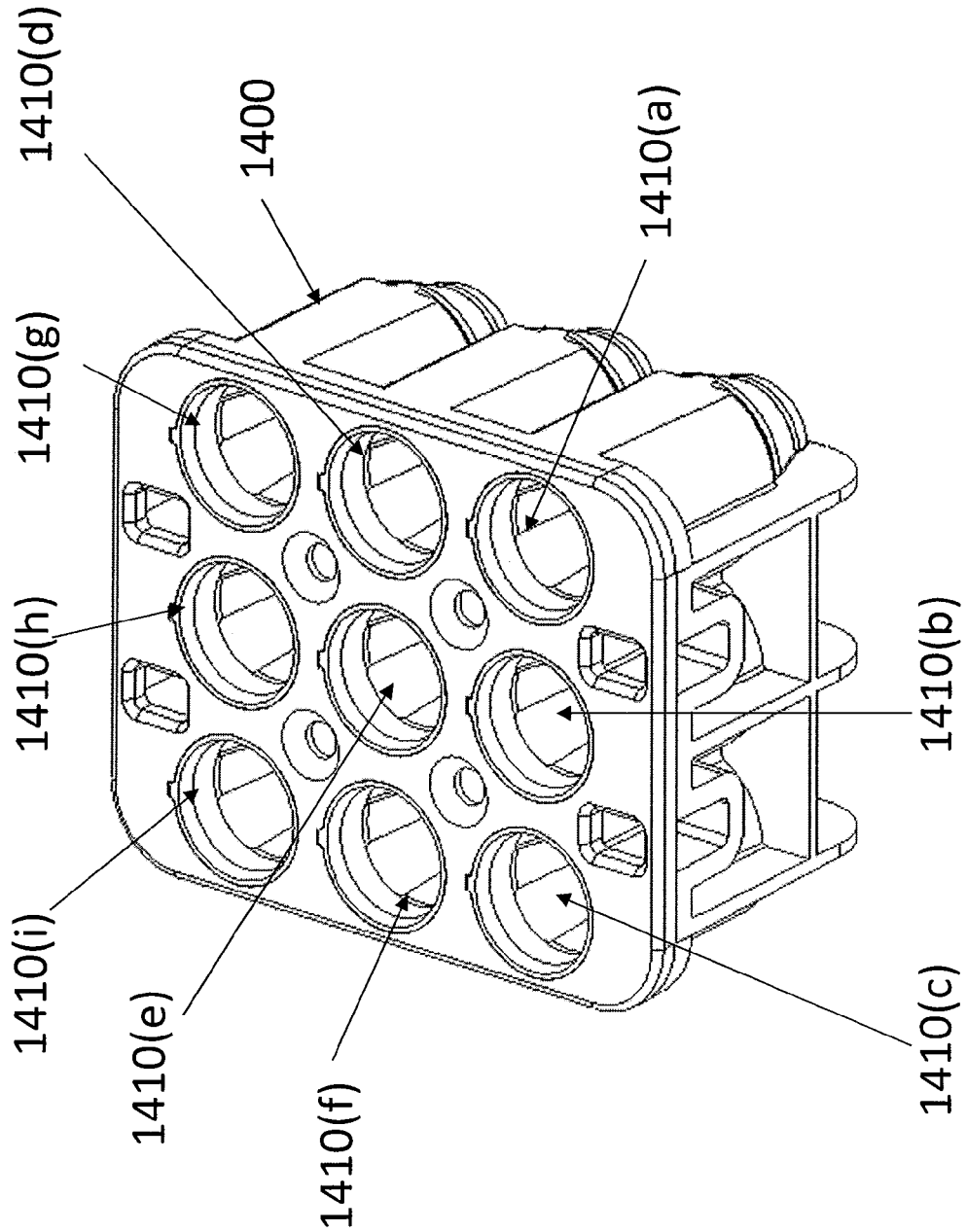
FIG. 16 shows an exemplary grid-like rack.
Figure 17:
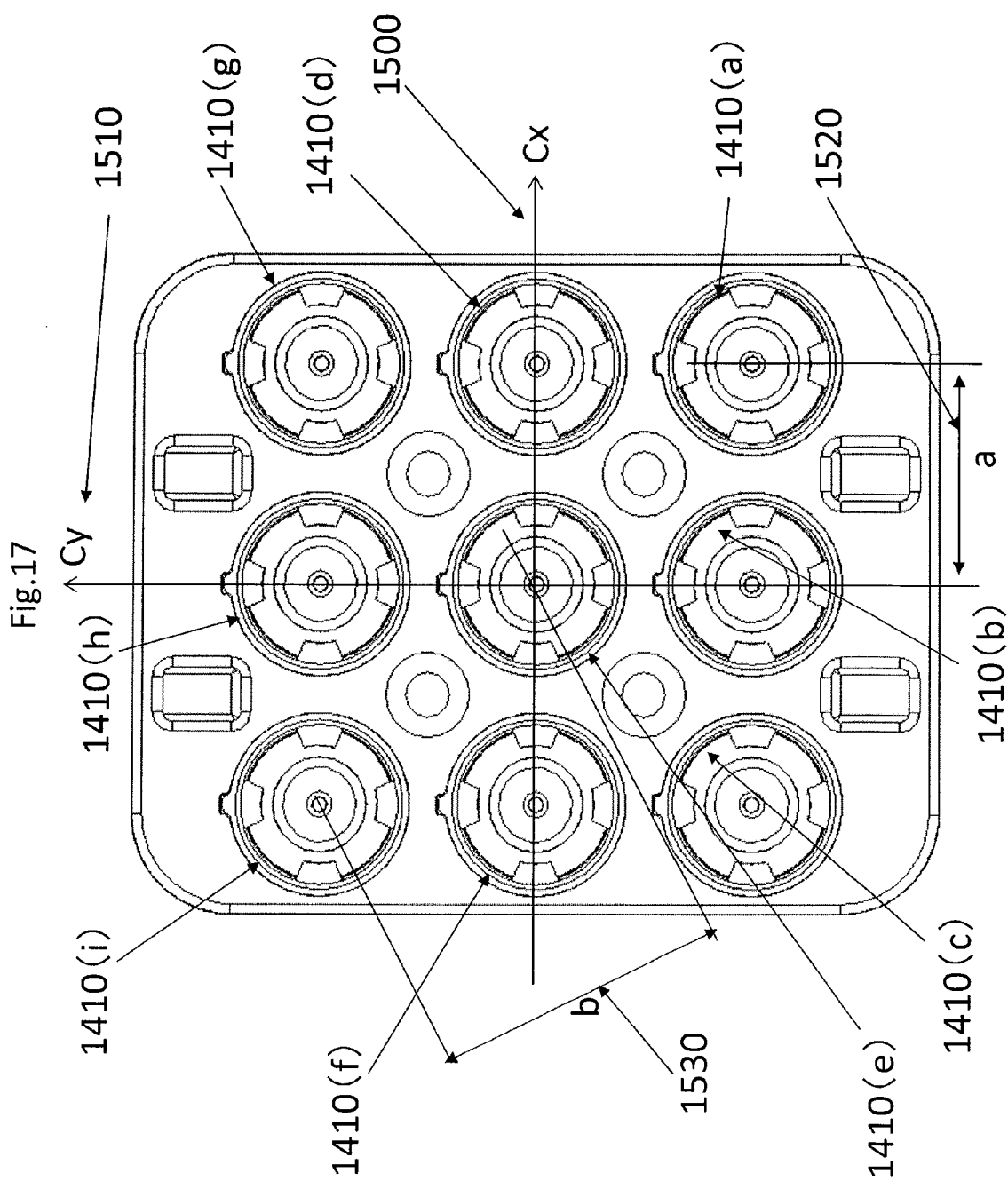
FIG. 17 shows an exemplary grid-like rack (plan view).

FIGS. 16 and 17 show a grid-like rack as an exemplary sample rack (grid-like rack) characterized by arraying sample holders in an m-by-n square grid pattern, m and n being each 3. Specifically, a grid-like rack 1400 according to this embodiment includes sample vessel mounting portions 1410(a) to (e) in which sample vessels are mounted. The sample vessel mounting portions 1410(a) to (e) are arrayed in three rows in a vertical direction (in a $C_y$-axis direction 1510 in FIG. 17) and in three columns in a crosswise direction (in a $C_x$-axis direction 1500 in FIG. 17). Thus, a total of nine sample vessel mounting portions is arrayed in a square grid pattern. Any other arrangement may be used as long as the holder or the like has the square grid pattern arrangement.

The grid-like rack 1400 exemplifies a case in which the $C_x$-axis direction 1500 is set to be opposite to the X-axis direction 001 and the $C_y$-axis direction 1510 is set to be the same as the Y-axis direction 002. Nonetheless, any other case may be possible as long as the grid-like rack faces forward and an angle formed between the $C_x$-axis direction 1500 and the X-direction 001 is any of 0°, 90°, 180°, and 270°.

An operation in which the gripper assembly 100 picks up a sample vessel 800 mounted in a specific sample vessel mounting portion 1410(e) on the grid-like rack 1400 will be described below. In this embodiment, it is assumed that the grid-like rack 1400 is loaded with the sample vessels 800.

FIGS. 18 to 21 are schematic views showing that the gripper assembly 100 is approaching the grid-like rack 1400. Steps in a sample vessel pickup motion will be described below.

1. First, the gripper assembly 100 is driven in the X-direction 001 and the Y-direction 002 by the X-Y-Z stage. When the central axis 110 of the sample transfer mechanism is substantially aligned with a central axis of the sample vessel mounting portion 1410(e) in which the sample vessel to be picked up is mounted, the movement of the chuck mechanism 200 in the X-direction 001 and the Y-direction 002 is stopped (accessing motion).

2. Thereafter, the gripping arms 160 are opened (opening motion).

Figure 18:
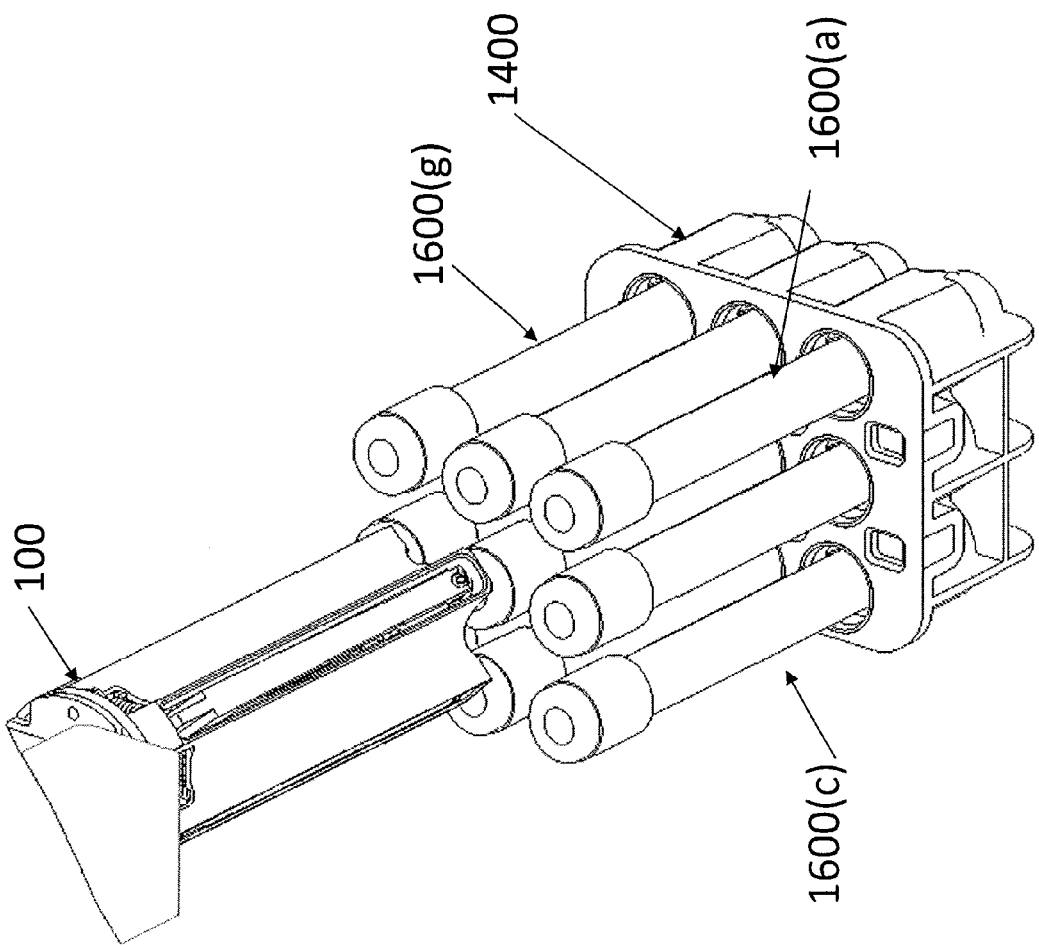
FIG. 18 shows a sample transfer mechanism during an approaching motion/retracting motion relative to the grid-like rack.
Figure 19:
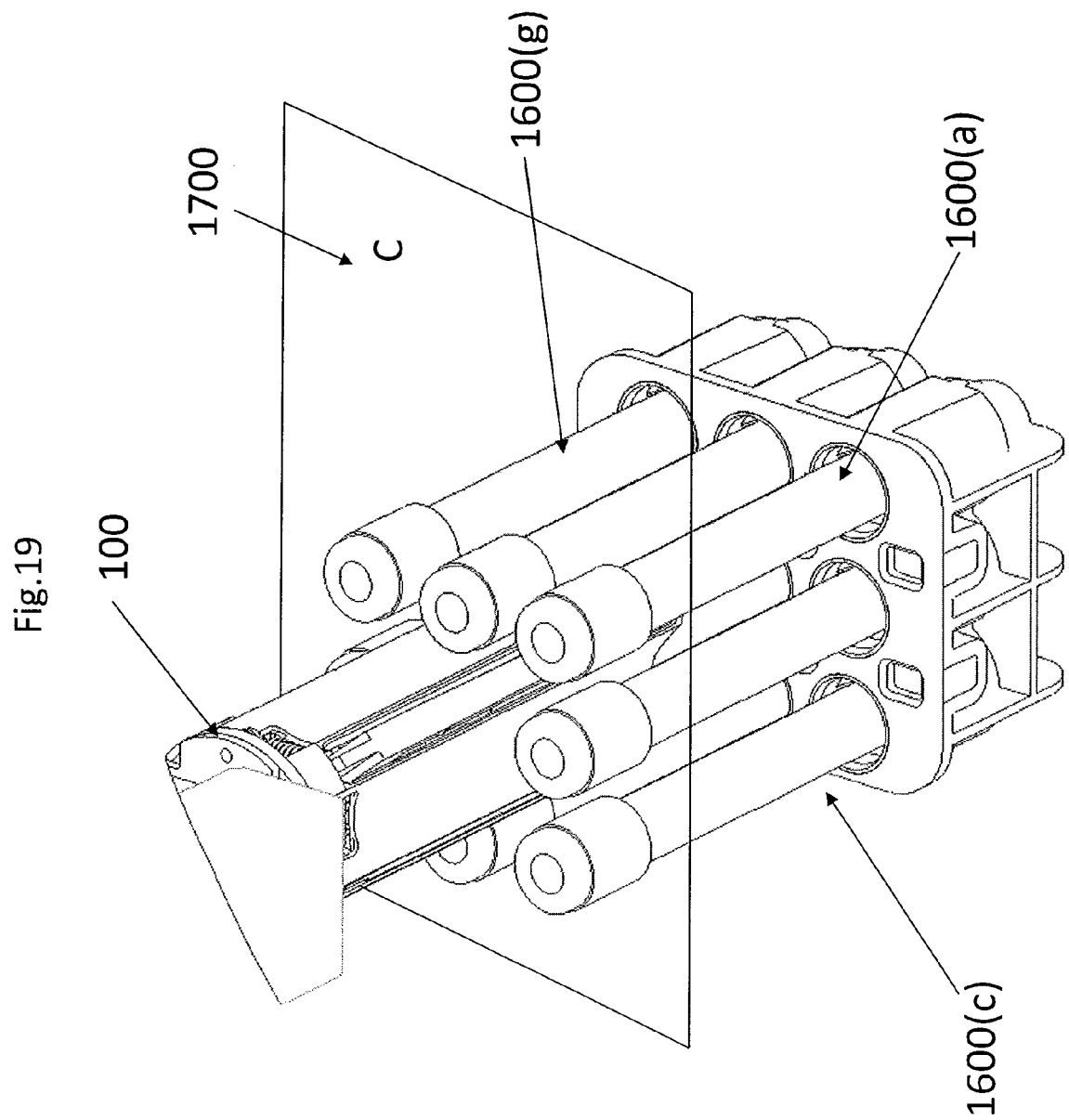
FIG. 19 shows the sample transfer mechanism that has completed approaching the grid-like rack.

3. Under this condition, the gripper assembly 100 is lowered in the Z-axis direction 120 as shown in FIG. 18. The movement in the Z-direction is stopped in a state where the sample vessel 800 mounted in the sample vessel mounting portion 1410(e) can be gripped (approaching motion) as shown in FIG. 19.

4. The gripping arms 160 are closed to grip and hold the sample vessel 800 (clamping motion).

Figure 21:
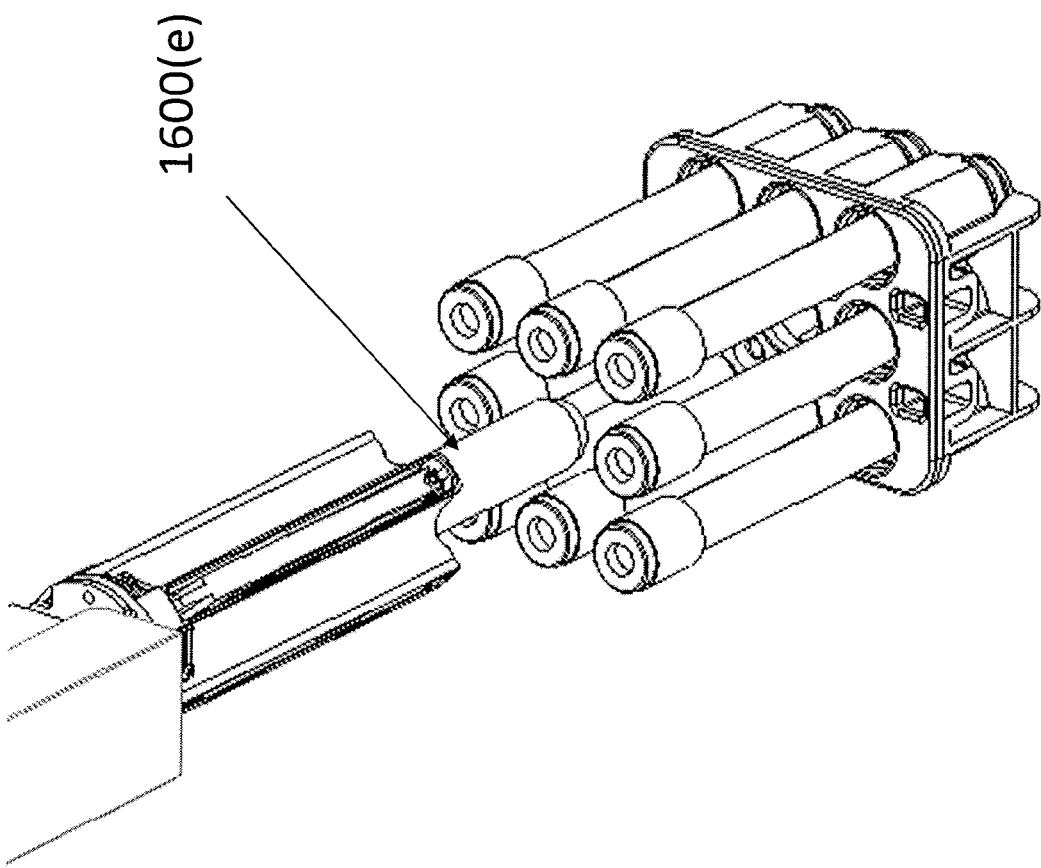
FIG. 21 shows a sample transfer mechanism having gripped a sample vessel during an approaching motion/retracting motion.

5. Under the above condition, the gripper assembly 100 is driven upwardly as shown in FIG. 21 (retracting motion).

In performing these steps, the present invention does not require that measurement of tilt or height of the sample vessel to be picked up be made.

Figure 20:
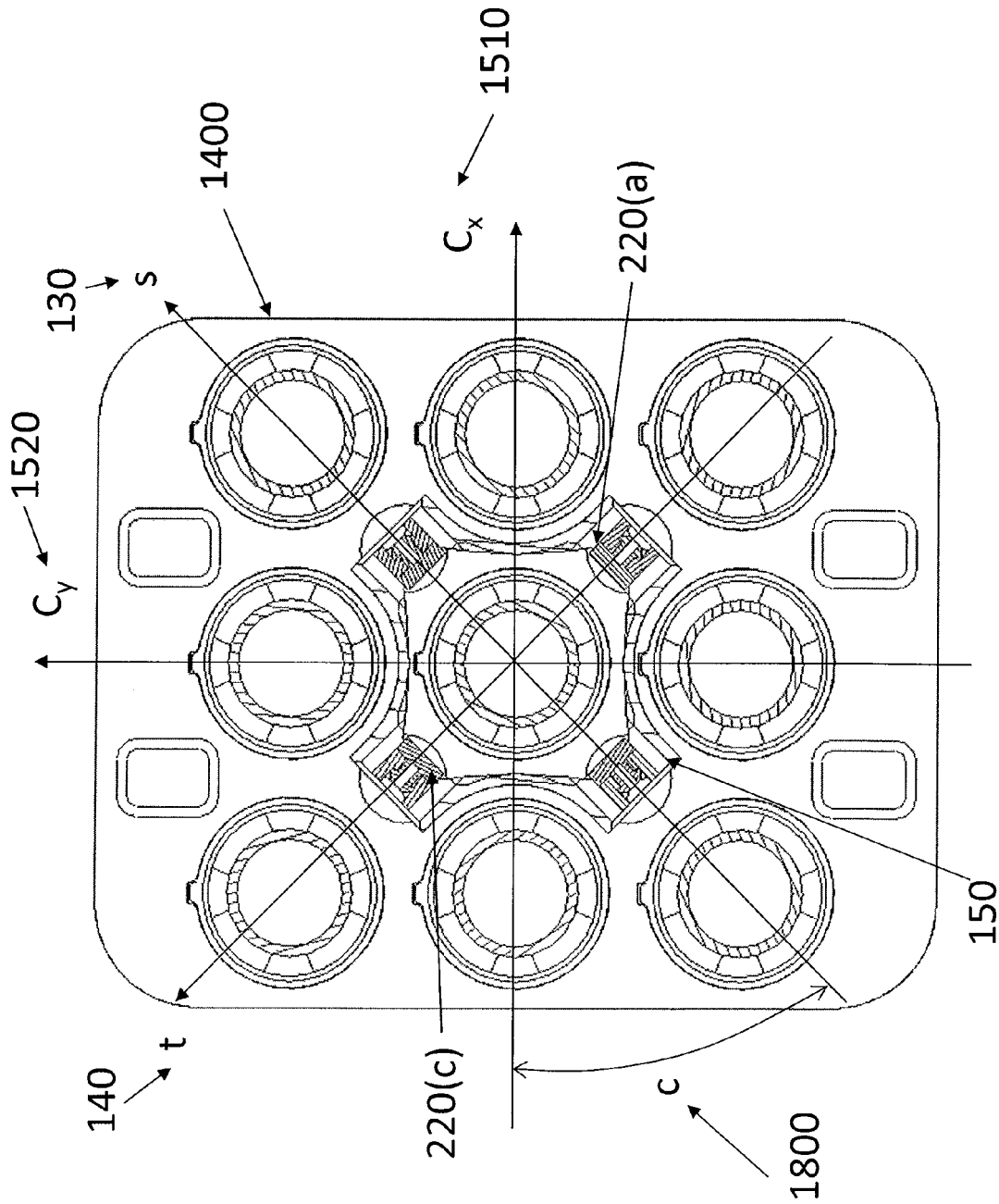
FIG. 20 is a cross-sectional view taken along plane C of FIG. 19.

FIG. 20 is a cross-sectional view taken along a plane C 1700 of FIG. 19. Now, consider a distance a 1520 between the sample vessel mounting portion 1410(e) to be accessed by the gripper assembly 100 and a sample vessel mounting portion closest thereto (e.g. 1400 (d)) and a distance b 1530 between the sample vessel mounting portion 1400 (e) to be accessed by the gripper assembly 100 and a sample vessel mounting portion second closest thereto (e.g. 1400 (i)). Since the sample vessel mounting portions are arrayed in a square grid pattern, the distance b is the square root of 2 as long as the distance a.

Meanwhile, the gripper assembly 100 is assembled, as described earlier, relative to the X-Y-Z stage 010, more specifically, such that the u-direction 140 extends in parallel with and opposite to the Z-direction 003 and the s-direction 120 and the t-direction 130 form an angle of 45 degrees relative to the X-direction 001 and the Y-direction 002, respectively. The grid-like rack is arranged as described earlier. Consequently, the four gripping arms 160 of the gripper assembly 100 are disposed at positions angled 45 degrees (see an angular dimension c 1800) relative to the grid axes Cx 1500 and Cy 1510 of the square grid-like arrangement of the vessels mounted on the vessel holder.

As a result, in both the approaching motion and the retracting motion, the gripping arms 160 are located in wide gap portions (distance b) relative to the four second closest sample vessel mounting portions. Additionally, the gripping arms are perpendicular to the horizon when fully opened. Space efficiency can therefore be utilized effectively, so that an occupied volume by the presence of the gripping arms 160 and the cover 150 does not reduce mountable density of sample vessels of the grid-like rack.

Additionally, the cover 150 according to the embodiment prevents the sample vessel from toppling over. Specifically, at timing at which the gripping arms do not hold any sample vessel during an approaching motion or a retracting motion, the sample vessel, should it tilt largely for some reason, has only to lean against the inner wall of the cover 150.

If the sample vessel held in the holder tilts largely in an approaching motion, the gripping arms 160 fail to grip the sample vessel properly in the related-art sample transfer mechanism. The sample transfer mechanism of the present invention, however, includes the cover 150 and grips the downward portion of the sample vessel. Even if the sample vessel tilts largely, as the approaching motion further progresses, the inner wall of the cover 150 serves as a guide for correcting the posture of the sample vessel, so that the sample vessel can be gripped in a straight position.

The cover 150 of this embodiment may have the recesses 340 formed in the outer wall thereof. In the sample transfer mechanism according to the embodiment of the present invention, the open/close direction of the gripping arms 160, specifically, the s-direction 120 and the t-direction 130 form an angle of 45 degrees relative to the grid axes Cx 1500 and Cy 1510 (see the angular dimension c 1800). In a condition in which the grid-like rack is being accessed, the recesses 340(a) to (d) are to be positioned between the sample vessel being accessed and each of all other sample vessels closest to the sample vessel being accessed. As a result, even if the sample vessels are densely populated on the holder, the recesses 340 in the cover 150 bypass adjacent sample vessels, so that unnecessary or accidental tension can be prevented from being applied to surrounding sample vessels. In addition, even if the sample vessel held on the holder is tilted, the cover 150 can correct the posture of the sample vessel 800.

In addition, the cover 150 of this embodiment may have the grooves 320 formed in the inner wall thereof, the grooves 320 corresponding in number with the gripping arms 160 for housing therein the gripping arms 160.

In this case, as described in "Structure of chuck mechanism" (see FIG. 4), preferably, when the gripping arms 160 are fully open, each of the gripping arms 160 is perpendicular to the upper end surface of the holder. Specifically, when the gripping arms 160 are open, all gripping arms 160 have at least leading end portions resting inside the grooves. When the sample transfer mechanism is made to approach the sample holder, therefore, the gripping arms 160 do not catch the sample vessel to be transferred or other sample vessels.

The leading end 330 of the cover of the embodiment may be disposed lower than the lower end of the gripping arms 160. Each of the notches at the leading end of the cover are rounded, chamfered several millimeters or radiused. Therefore, even if the leading end of the cover contacts another sample vessel 800 mounted in another sample vessel mounting portion 1410 (b) adjacent to the sample vessel mounting portion 1410 (e) in which the sample vessel 800 to be gripped is mounted, tension applied to the sample vessel 800 is far smaller than that applied when the gripping arms 160 directly contact, so that the sample vessel 800 can be prevented from toppling over or being damaged.

Figure 15:
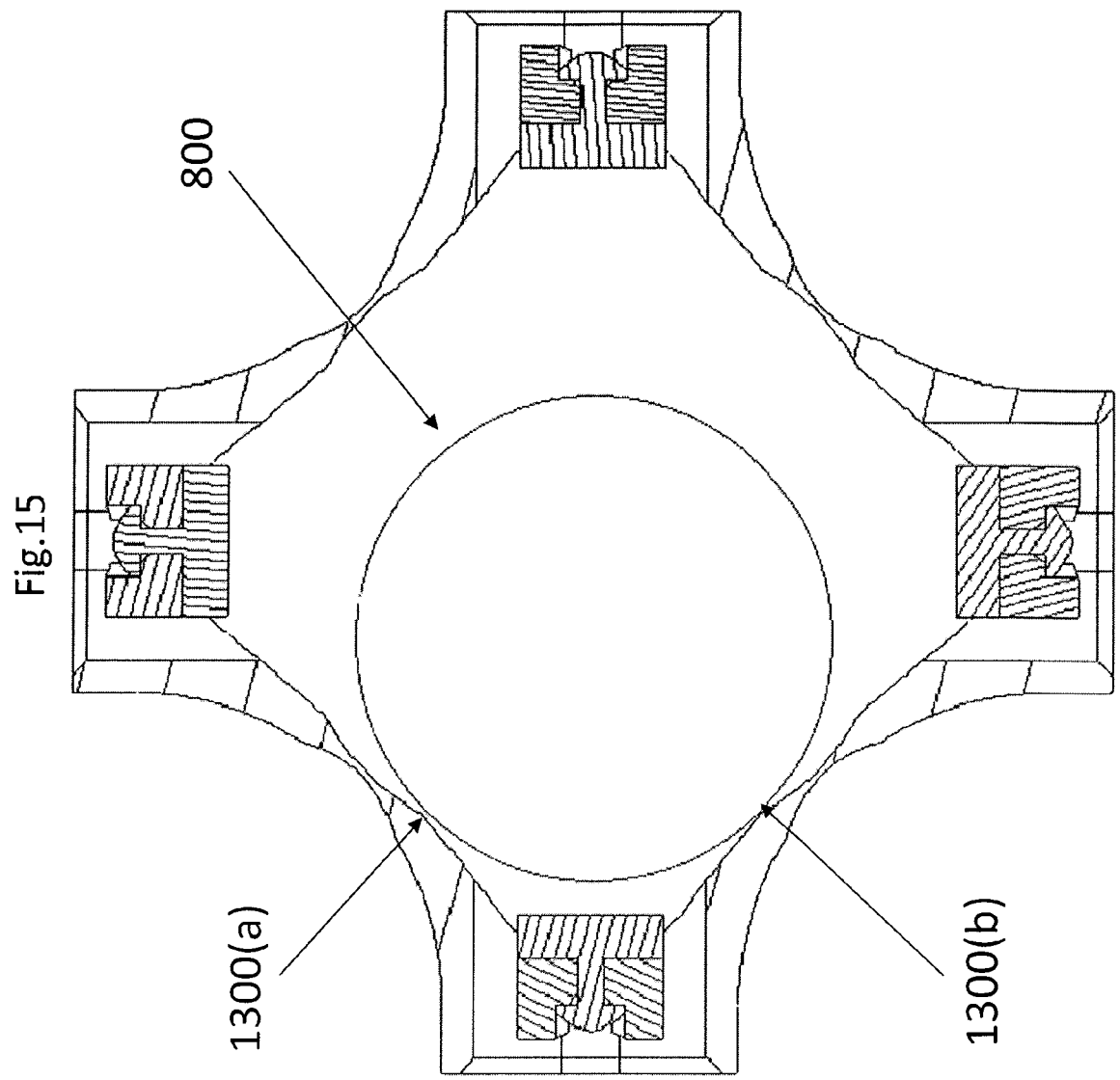
FIG. 15 shows, in the same cross section as that in FIG. 14, a state where the sample vessel is closest to a rubber pad side at a leading end of a gripping arm.

As another effect, when, for example, relative positions of the sample vessel 800 and the chuck mechanism 110 are deviated in the X-Y direction for some reason with the gripping arms 160 opened to release the sample vessel 800, resulting in the sample vessel 800 being closest to the rubber member 220 at the leading end of the gripping arm 160 (see FIG. 15), the sample vessel 800 has contact points 1300(a), (b) (normally a point contact, a line contact in the worst case) with the inner wall of the cover and does not tilt any more. Furthermore, the gripping arms 160 have the leading end portions resting inside the grooves 320 formed in the cover wall surface. When the gripping arms 160 are open, therefore, the outer surface of the sample vessel 800 does not contact the rubber members 220 at the leading ends of the gripping arms 160, so that the sample vessel 800 can be prevented from toppling over.

From the foregoing, even in a case in which the gripping arms lower over a long distance to thereby approach the sample vessel, the cover serves as a guide for guiding the gripping arms downwardly, enabling smooth lowering motion and downward gripping. This basically eliminates the need for acceleration or deceleration other than that which is inevitably performed during stopping or starting the actuator. Alternatively, the range of acceleration or deceleration may be even smaller, thus enabling an approaching motion and a retracting motion at high speeds.

Compared with the related-art method that determines the height of the sample vessel to thereby change the lowering stroke, sensor detection is not required, which reduces time loss and device cost. Downward gripping does not necessarily result in longer lowering/raising distance. Should the lowering distance be long, high-speed vertical movement is possible even in the range in which the lower end of the gripping arm 160 is positioned downwardly of the upper bottom of the sample vessel (there is no harmful effect from the high-speed movement), which minimizes time loss effect. Further, there is no need to change the lowering motion according to the height of the sample vessel, which simplifies control of the sample transfer mechanism.

The cover 150 also has an effect of correcting the posture of the sample vessel to a vertical position. Enhanced safety can thus be achieved regardless of the type of sample vessel and the effect of posture correction enables accurate transfer processing.

The above effect also permits downward gripping, which enables reliable gripping and transfer regardless of the type of sample vessel. Specifically, the gripping arms can be lowered to a position at which any type of sample vessel can be gripped. This leads to a reduced risk that the sample vessel will topple over or drop off during transfer.

Second Embodiment

A second embodiment of the present invention will be described below as an exemplary placing motion in which sample vessels 800 are placed in a grid-like rack 1400 on which the sample vessels 800 can be mounted in a square grid pattern. Accordingly, like or corresponding parts are identified by the same reference numerals as those used in the first embodiment and descriptions for those parts will be omitted.

An exemplary case to be described below is sample transfer means that has already clamped a sample vessel 800 accesses a sample vessel mounting portion 1410(*e*) in which a sample vessel is not mounted and places the sample vessel 800 in the sample holder.

Steps for placing the sample vessel will be first described.

1. When a central axis 110 of the sample transfer device is substantially aligned with a central axis of the sample vessel mounting portion 1410(*e*) by an X-Y-Z stage 010, motions of a chuck mechanism 200 in the X-direction 001 and the Y-direction 002 are stopped (accessing).

2. Thereafter, with the sample vessel 800 clamped, the chuck mechanism 200 is lowered in the Z-axis direction 120 and brought to a stop when the bottom of the sample vessel 800 contacts the bottom in the sample vessel mounting portion 1410(*e*) (approaching).

3. Gripping arms 160 are opened under this condition to release the sample vessel 800.

4. Thereafter, with the gripping arms 160 opened, the gripper assembly 100 is raised in the Z-direction 003 to thereby retract the gripping arms 160 upwardly (retracting).

In the placing motion, too, an outer wall and an inner wall of a cover 150 serve as guides to enable a smooth lowering motion as in the first embodiment. When the gripping arms 160 are lowered over a long distance, a deceleration range can be made short. Not only that, even with the gripping arms 160 being lowered over a long distance, the cover achieves an effect of, for example, correcting posture of the sample vessel.

In addition, the placing motion involves opening of the gripping arms 160 with the gripping arms 160 in a lowered position. When the gripping arms 160 are to be opened, opening the gripping arms 160 at high speed should be advantageous in terms of throughput. If urged gripping arms 160 contact a surrounding sample vessel, however, there is a risk that the surrounding sample vessel will be tilted or flicked off through momentum. However, the structure in which the gripping arms 160 when fully opened are substantially vertical and the grooves in the cover eliminate the risk that the gripping arms 160 will contact the surrounding sample vessel even when the gripping arms 160 are to be opened after the approaching motion (e.g. during a placing motion). This allows the gripping arms 160 to be opened at high speed (no harmful effect from opening the gripping arms 160 at high speed). For an approaching motion for the subsequent placing motion with the sample vessel gripped in a slightly tilted position, given the same tilted angle, the shorter the distance between the gripping position and the lower bottom of the sample vessel, the smaller the lower bottom of the sample vessel is deviated from the center position. Downward gripping therefore achieves higher positioning accuracy than upward gripping.

The sample holder or the like that handles different types of sample vessels includes a sample vessel mounting portion in which a sample vessel is mounted and that has a structure that allows sample vessels having different cross-sectional diameters to be mounted. A typical structure includes a sample vessel mounting portion having an outline designed largely so as to allow a sample vessel having the largest diameter to be mounted. The structure further includes an internal mechanism that holds a sample vessel with an elastic force of an elastic body, such as a spring, so that a sample vessel having a diameter smaller than the foregoing sample vessel can be held therein. When a sample vessel is to be mounted, therefore, the sample vessel needs to be pushed into the sample vessel mounting portion with a force to resist resistance, such as a frictional force, occurring as a result of a contact with the elastic body. The resistance from the holder side should ideally be applied at this time in a perpendicular direction only. In reality, however, as a result of the sample vessel being slightly tilted upon insertion and several other phenomena, torque is applied to the gripping position of the sample. This torque is greater with greater distances between a portion of the sample vessel in contact with the sample holder and the gripping portion. The torque affects less in downward gripping and the downward gripping enables even more stable placing motion.

Similarly, when a placing motion is performed in the downward gripping condition, the distance from the gripping position to the lower bottom of the sample vessel is shorter than in upward gripping. Should the leading end of the sample vessel contact an edge of a surrounding sample vessel or a sample vessel mounting portion of the holder or the like in a lowering stroke, therefore, torque applied to the gripping position is smaller than in upward gripping. There is therefore a low risk of, for example, dropping even under the foregoing situations.

The sample vessel can be reliably released during a placing motion. For example, the sample vessel 800 may be affixed with a seal, such as a bar code label, for identifying the sample housed therein. The seal may cause the surface of the sample vessel to develop an area having adhesion. In the related-art sample transfer mechanism, even when the gripping arms 160 are opened to perform the releasing motion, adhesion between the sample vessel 800 and the rubber member (e.g. 220(*d*)) at the leading end of a gripping arm 160 may prevent the gripping arm 160 from separating from the sample vessel 800. In the gripper assembly 100 according to this embodiment, the cover has the grooves 320 formed in its inner wall and the gripping arms 160 in the open position can fit in the grooves 320. Perpendicular resistance from the contact points 1300(*a*), (*b*) relative to the cover inner wall allows the sample vessel 800 to be reliably released from the rubber member 220(*d*) at the leading end of the gripping arm. Moreover, the cover 150 and the sample vessel 800 each have an axially symmetrical shape, so that a contact area between the cover inner wall and the sample vessel 800 is small. Understandably, the sample vessel 800 is less likely to be stick to the cover inner wall when separated from the rubber member 220 at the leading end of the gripping arm 160.

As such, lowering the gripping arms 160 down to an area at which the lower ends of the gripping arms 160 are considerably lower than the upper end of the sample vessel does not result in reduced processing speed (as a result of, for example, reduced lowering speed) or an increased risk of accident. This enables the downward gripping as described in "Gripping position of sample vessel". As a result, as described in "Gripping position of sample vessel", being able to grip at any position at which any sample to be handled can be gripped, more precisely, lowering down to a position at which any sample to be handled can be gripped leads to prevention of reduced throughput or a risk of toppling over. Compared with the related-art system that determines the height of the sample vessel and changes the lowering stroke according to the length of the sample vessel, therefore, time loss involved in, for example, sensor detection can be eliminated.

Downward gripping does not necessarily result in a longer lowering stroke. Should the lowering stroke become long, high-speed vertical movement is enabled even in a range in which the lower ends of the gripping arms 160 are located downwardly of the upper bottom of the sample vessel (no harmful effect from the high-speed movement). This eliminates the need for selecting a specific lowering distance from among a large number of options of distances, thus facilitating control.

Compared with the related-art sample transfer mechanism having no cover 150, the sample transfer mechanism according to the embodiment of the present invention offers even more enhanced safety because of no risk of contact of the gripping arms with the sample vessel or the like regardless of the gripping position and is capable of transfer with high repeatability because of the effect from posture correction.

Third Embodiment

A third embodiment of the present invention will be described below. A gripper assembly 100 according to the third embodiment is incorporated in a sample transport mechanism capable of transporting a sample rack having a plurality of sample vessel mounting portions arrayed in a row. The third embodiment will be described as an exemplary picking motion in which a sample vessel loaded in the sample rack is picked up. Accordingly, like or corresponding parts are identified by the same reference numerals as those used in the first embodiment and descriptions for those parts will be omitted. A sample rack having five sample holders arrayed in a row (five-vessel transport rack) is commonly used for the sample rack and this embodiment will be described for an exemplary picking and placing motion relative to the five-vessel transport rack.

Figure 22:
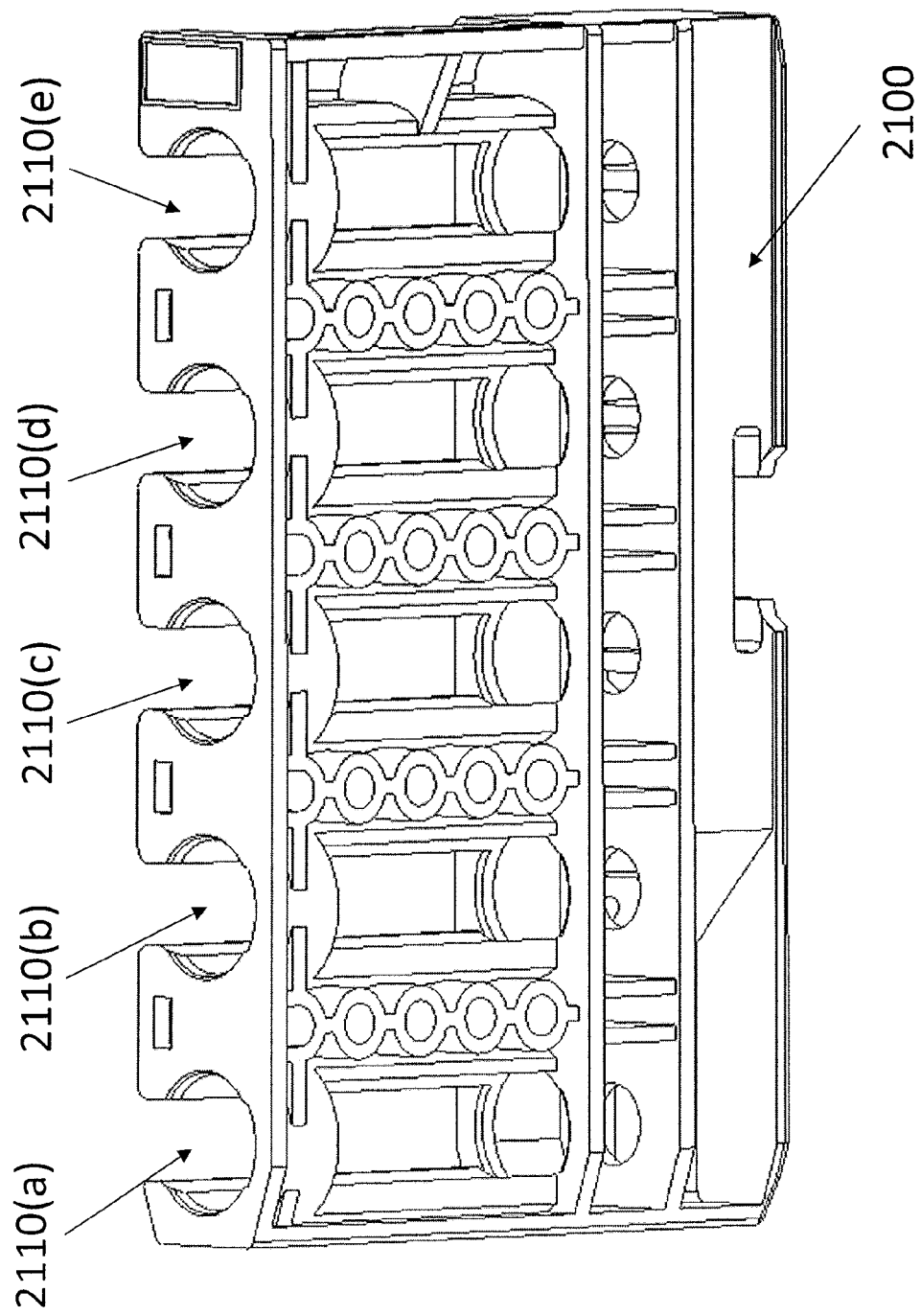
FIG. 22 is an outline view showing a five-vessel transport holder.

FIG. 22 is an outline view showing a five-vessel transport rack 2100 according to this embodiment. The five-vessel transport rack 2100 has five sample vessel mounting portions 2110(a) to (e). FIG. 22 schematically shows a gripper assembly 100 that has completed approaching the five-vessel transport rack 2100 in which all required sample vessels 800 have been mounted. The sample vessels are denoted 2210(a) to (e) in sequence from left to right and mounted, respectively, in the sample vessel mounting portions 2110(a) to (e).

An operation of the gripper assembly 100 will be exemplarily described in which the gripper assembly 100 accesses the sample vessel mounting portion 2110(c) of interest and sample transfer means performs a picking motion. It is assumed in this case that a chuck mechanism 200 of the sample transfer means is yet to clamp the sample vessel.

Figure 23:
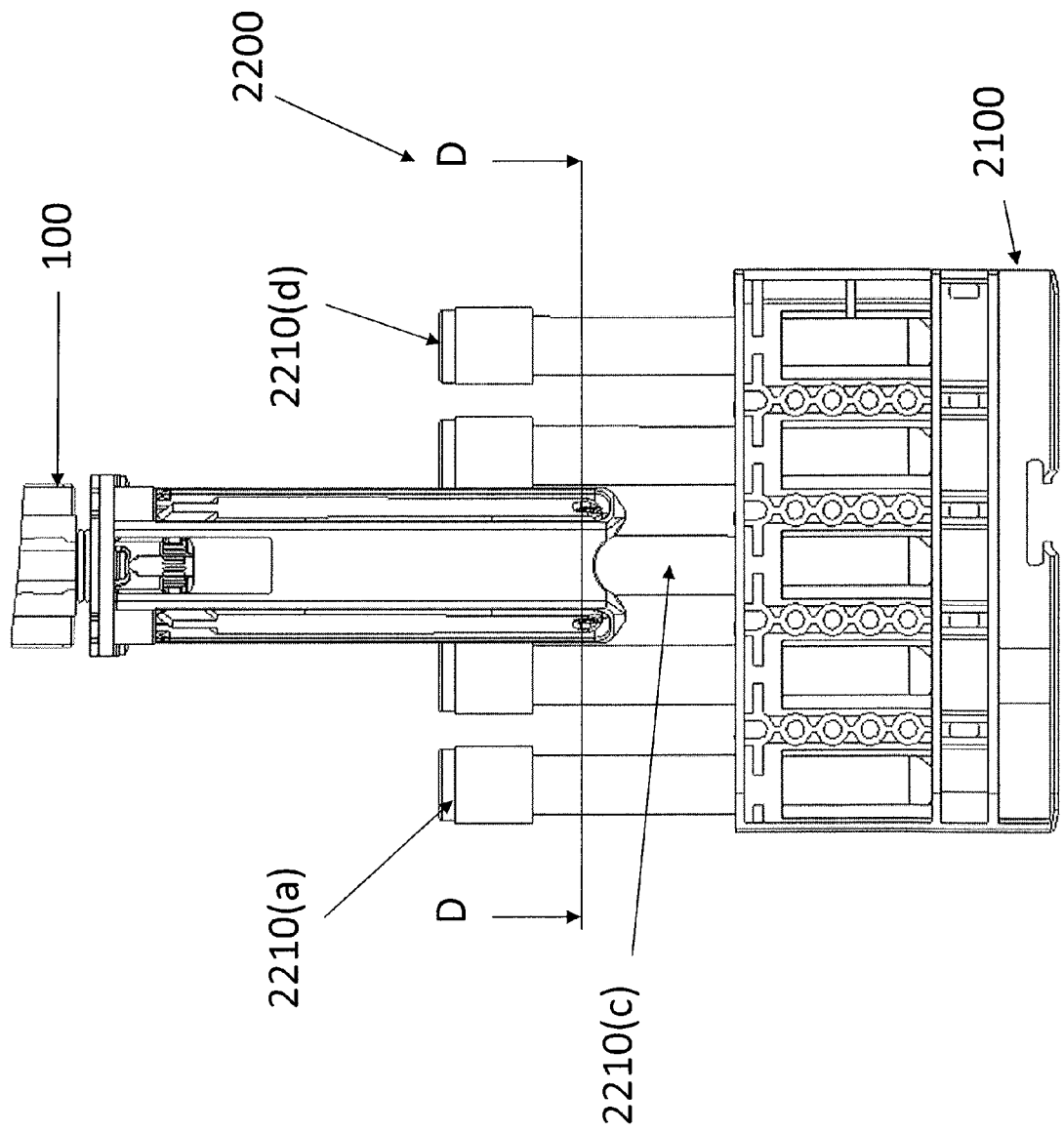
FIG. 23 shows an illustration showing a sample transfer mechanism that has approached the five-vessel transport holder.

First, an X-Y-Z stage drives the gripper assembly 100 in the X-direction 001 and the Y-direction. When a central axis 110 of the sample transfer mechanism is substantially aligned with a central axis of the sample vessel mounting portion 2210(c), the movements of the sample chuck mechanism 200 in the X-direction 001 and the Y-direction 002 are brought to a stop. Gripping arms 160 in an open position are thereafter lowered in the Z-axis direction 120. When the gripping arms 160 are capable of gripping the sample vessel 2120(c) as shown in FIG. 23, the gripping arms 160 are stopped from moving in the Z-direction. The sample vessel of interest is thereafter transferred through a subsequent upward motion in the Z-direction with the sample vessel 2120(c) gripped in place.

Figure 24:
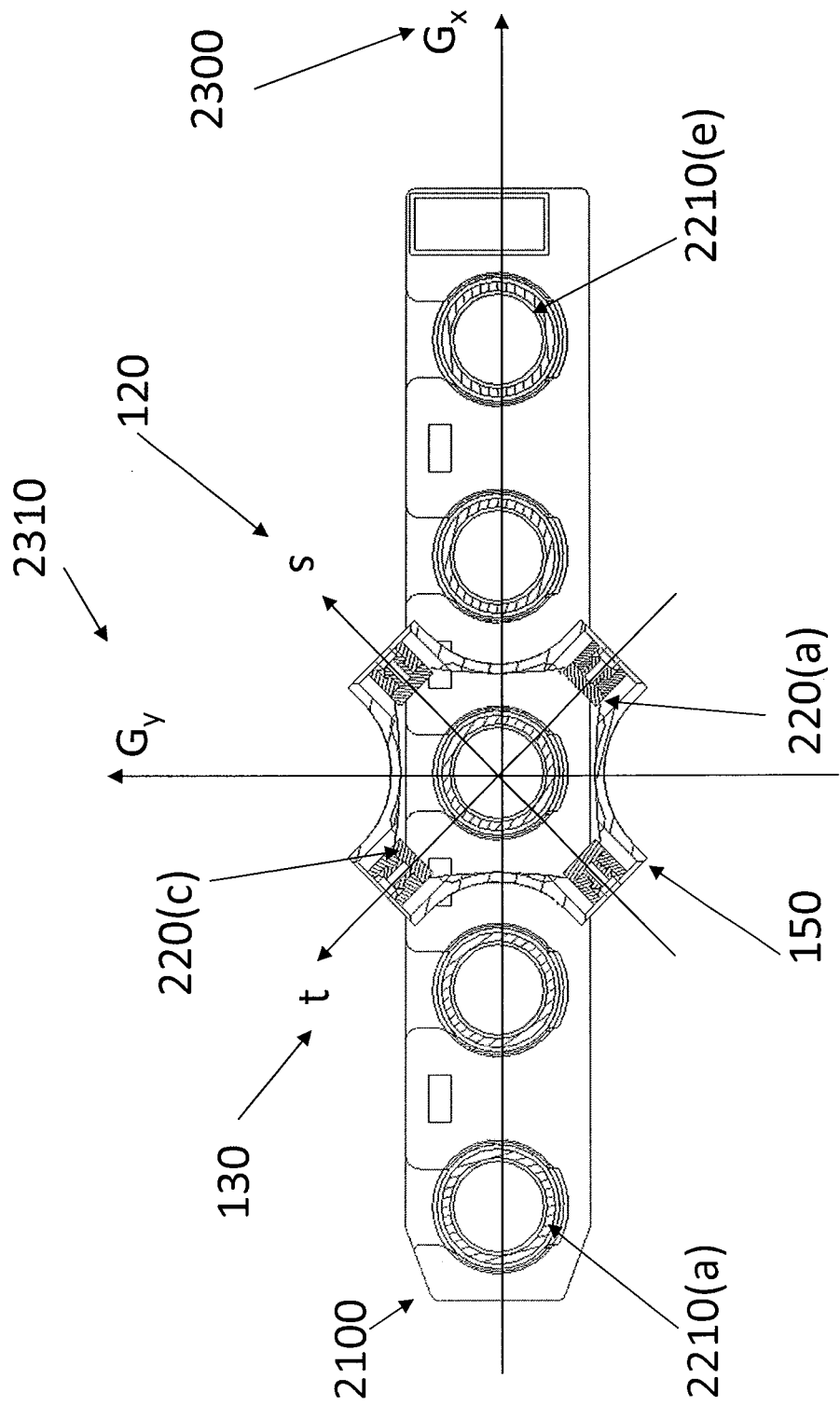
FIG. 24 is a cross-sectional view taken along line D-D of FIG. 23.

In this embodiment, the sample vessels 2210(b), (d) adjacent to the sample vessel 2210(c) of interest are present in one direction only (a $G_x$-axis direction 2300 in FIG. 24). Recesses 340 formed in the cover outer wall have only to be formed on both sides in the $G_x$-direction 2300. Specifically, recesses 340 in a $G_y$-direction 2310 are not necessarily required. If, for example, a step of picking up a sample vessel from the grid-like rack 1400 is inserted before the transfer of the sample vessel onto the five-vessel transport rack 2100, however, the recesses 340 in the $G_y$-direction 2310, if available, should be beneficial.

In addition, two gripping arms 160 are sufficient for picking up the sample vessel. This is advantageous in simplifying the structure of the gripper assembly 100 and reducing the device cost. Further, if a working range of the gripping arms 160 is provided in the $G_y$-direction 2310, a sample gripping motion is enabled without having to consider adjacent sample vessels.

The gripping arms 160, if there are provided four of them, enable steady gripping of the sample vessel. In this case, the four gripping arms 160 are disposed such that an t-axis direction 130 and a s-axis direction 120 in which the gripping arms 160 are open form an angle of 45 degrees relative to the $G_x$-axis direction 2300 and the $G_y$-axis direction 2310. Such disposition results in open gripping arms 160 not entering areas adjacent to the adjacent sample vessels, which enhances mounting density of the sample vessels.

Fourth Embodiment

Effects, such as avoidance of contact between the arm and the sample vessel to be picked and placed and peeling of a pad from the surface of the sample vessel, are also achieved in, for example, the picking and placing motion relative to a single-vessel transport holder such as that shown in FIG. 10.

Additionally, the sample vessel is transferred with its upper side bitten inside the cover 150. Should an accident involving a contact by an operator with the gripper assembly 100 of the transfer mechanism during a transfer operation occur, another conceivable effect would be a low risk of dropping off from a contact with the cover 150 rather than with the sample vessel itself.

DESCRIPTION OF REFERENCE NUMERALS

001: X-direction
002: Y-direction
003: Z-direction
010: Transport mechanism for sample transfer mechanism in the embodiment of the present invention (X-Y-Z stage)
100: Gripper assembly of sample transfer mechanism
101: Base section of gripper assembly of sample transfer mechanism
110: Central axis of sample transfer mechanism (which is datum axis)
120: s-direction
130: t-direction
140: u-direction
150: Cover
160(a), (b), (c), (d): Gripping arm
161: Fixture
162(a), (b), (c), (d): Connection between gripping arm and fixture (part of reference numerals not shown in figures for ease of viewing)
170(a), (b), (c), (d): Screw (part of reference numerals not shown in figures for ease of viewing)
200: Chuck mechanism
210(a) to (d): Protrusion
220(a) to (d): Rubber member
230: Translation cam
231: Follower (a), (b), (c), (d) (part of reference numerals not shown in figures for ease of viewing)
232: Shoulder
300: Central axis of cover (which is datum axis)

310: Line A-A
320(a) to (d): Groove
330: Opening portion
340(a) to (d): Recess
500: Hollow
510: Cover inner wall
600(a) to (d): Chamfered shape
610: Radiused part (inside)
620(a) to (d): Radiused part (outside)
700, 701: Gripper assembly (excluding cover)
710: Short sample vessel
711: Long sample vessel
720, 721: Single-vessel transport holder
730: Grippable position of short sample vessel
731: Grippable position of long sample vessel
740, 741: Cap
750: Reference plane
800: Sample vessel
900: Line B-B
1300(a), (b): Point of contact with cover inner wall
1400: Grid-like rack
1410(a) to (i), 2110(a) to (e): Sample vessel mounting portion
1500: $C_x$-axis
1510: $C_y$-axis
1520: Distance a
1530: Distance b
1600(a) to (g): Sample vessel mounted in grid-like rack (part of reference numerals not shown in figures for ease of viewing)
1700: Plane C
1800: Angle formed between X-axis and $C_x$-axis (angular dimension c)
2100: Five-vessel transport rack
2200: Line D-D
2210 (a) to (f): Sample vessel (a, b, c, d, e, f in sequence from left to right FIG. 20; part of reference numerals not shown in FIGS.
2020: Single-vessel holder outer wall
2300: $G_x$-axis direction
2310: $G_y$-axis direction
2500: Sample preprocessing system
2510 (a) to (c): Sample transfer mechanism mounted on sample preprocessing system

The invention claimed is:

1. A sample transfer mechanism configured to carry out an arbitrary sample vessel of a plurality of sample vessels each having an opening portion, a bottom portion, and a body portion of a plurality of types of different lengths, from a sample vessel holder and configured to carry an arbitrary sample vessel holder, the sample transfer mechanism comprising:
   a gripper assembly equipped with a plurality of openable gripping arms that grip the body portion of the sample vessels having the plurality of types of different lengths;
   a transport mechanism that moves the assembly to a predetermined position relative to a sample vessel to be gripped;
   a covering assembled in the gripper assembly having an inner wall having one or more grooves covering the outside of respective gripping arms, and in a state in which the gripping arms are opened, and a lower end disposed downwardly of the leading end portions of the gripping arms; and
   a control mechanism that controls the transport mechanism such that a gripping position at which the gripping arms grip the sample vessel is identical among the sample vessels having the plurality of types of different lengths.

2. The sample transfer mechanism according to claim 1, wherein
   the covering has a rounded lower end.

3. The sample transfer mechanism according to claim 1, wherein
   the covering has an outer wall having recesses having a shape that corresponds to the outer shape of the sample vessels adjacent to the particular sample vessel to be carried on the sample vessel holder.

4. The sample transfer mechanism according to claim 1, wherein
   in the state in which the gripping arms are opened and the gripping arms engage with respective grooves, the inner wall of the covering contacts the body portion of the sample vessel.

5. The sample transfer mechanism according to claim 3, wherein
   the holder holds a plurality of sample vessels including a first sample vessel to be gripped and a second sample vessel disposed closest to the first sample vessel, and
   the transport mechanism moves the gripper assembly so that the recesses provided on the outer wall of the covering is positioned to partition between the first sample vessel and the second sample vessel.

6. The sample transfer mechanism according to claim 1, wherein
   the holder holds in the plurality of sample vessels including a first sample vessel to be gripped in a grid pattern, a second sample vessel disposed closest to the first sample vessel, and a third sample vessel disposed second closest to the first sample vessel, and
   the transport mechanism moves the gripper assembly so that the gripping arms are located between the first sample vessel and the third sample vessel.

7. A sample processing apparatus comprising,
   a plurality of processing units including a processing unit having the sample transfer mechanism according to claim 1; and
   a sample transport mechanism that transports sample vessels to and from the processing unit.

8. The sample processing apparatus according to claim 7, wherein
   the processing unit is at least one of a loading unit that transfers a plurality of sample vessels loaded onto an outside tray to another sample vessel holder, a storage unit that stores a sample vessel that has undergone processing in the sample processing apparatus in another tray for unloading outside the sample processing apparatus, and a centrifugal separation unit that reloads a sample vessel transported in a condition of being mounted in the holder onto amptjer cemtrofugal separation holder dedicated to centrifugal separation.

9. The sample transfer mechanism according to claim 1, comprising:
   a translation cam that opens and closes the gripping arms, wherein
   the gripping arms are opened to an angle that varies according to an amount of movement of the translation cam.

10. A sample processing apparatus comprising:
    a plurality of processing units including a processing unit having the sample transfer mechanism according to claim 2; and
    a sample transport mechanism that transports sample vessels to and from the processing unit.

11. A sample processing apparatus comprising:
a plurality of processing units including a processing unit having the sample transfer mechanism according to claim 3; and
a sample transport mechanism that transports sample vessels to and from the processing unit.

12. A sample processing comprising:
a plurality of processing units including a processing unit having the sample transfer mechanism according to claim 4; and
a sample transport mechanism that transports sample vessels to and from the processing unit.

13. A sample processing comprising:
a plurality of processing units including a processing unit having the sample transfer mechanism according to claim 5; and
a sample transport mechanism that transports sample vessels to and from the processing unit.

14. A sample processing apparatus comprising:
a plurality of processing units including a processing unit having the sample transfer mechanism according to claim 6; and
a sample transport mechanism that transports sample vessels to and from the processing unit.

* * * * *